US007514413B2

(12) United States Patent
Martin et al.

(10) Patent No.: US 7,514,413 B2
(45) Date of Patent: *Apr. 7, 2009

(54) IN-VIVO ENERGY DEPLETING STRATEGIES FOR KILLING DRUG-RESISTANT CANCER CELLS

(75) Inventors: Daniel S. Martin, Pound Ridge, NY (US); Joseph R. Bertino, Branford, CT (US); Jason Koutcher, New Rochelle, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/518,003

(22) PCT Filed: Jun. 13, 2003

(86) PCT No.: PCT/US03/18716

§ 371 (c)(1),
(2), (4) Date: Mar. 14, 2005

(87) PCT Pub. No.: WO03/105862

PCT Pub. Date: Dec. 24, 2003

(65) Prior Publication Data

US 2005/0159387 A1 Jul. 21, 2005

Related U.S. Application Data

(63) Continuation-in-part of application No. 10/172,346, filed on Jun. 13, 2002, now Pat. No. 7,381,713.

(51) Int. Cl.
*A61K 31/70* (2006.01)
*A61K 31/66* (2006.01)
*A61K 31/505* (2006.01)
*A61K 31/185* (2006.01)

(52) U.S. Cl. ............................ 514/34; 514/45; 514/75; 514/269; 514/553

(58) Field of Classification Search .................. 514/45, 514/269; 536/27.21; 546/310, 348; 562/8, 562/11, 571, 533; 564/47, 112–3; 568/926
See application file for complete search history.

(56) References Cited

U.S. PATENT DOCUMENTS 5,641,670 A 6/1997 Treco et al.
2003/0139331 A1 * 7/2003 Martin et al. .................. 514/12

FOREIGN PATENT DOCUMENTS

WO WO93/23014 A1 * 11/1993
WO WO 93/23014 A1 * 11/1993
WO PCT/US01/46886 12/2001
WO WO 02/45720 A1 6/2002

WO PCT/US03/18716 6/2003

OTHER PUBLICATIONS

Stolfi et al., "Biochemical Modulation of Tumor Cell Energy: Regression of Advanced Spontaneous Murine Breast Tumors with a 5-Fluorouracil-containing Drug Combination," *Cancer Research*, 52(15), 4074-4081 (Aug. 1, 1992).*
Colofiore et al., "Biochemical Modulation of Tumor Cell Energy IV. Evidence for the Contribution of Adenosine Triphosphate (ATP) Depletion to Chemotherapeutically Induced Tumor Regression," *Biochemical Pharmacology*, 50(11), 1943-1948 (Nov. 27, 1995).*
Martin et al. (III), "Marked Enhancement in vivo of Paclitaxel's (Taxol's) Tumor-Regressing Activity by ATP-Depleting Modulation," *Anti-Cancer Drugs*, 7, 655-659 (1996).*
Koutcher et al., "Radiation Enhancement by Biochemical Modulation and 5-Fluorouracil," *Intl. J. Radiation Oncology Biology Physics*, 39(5), 1145-1152 (Dec. 1, 1997).*
Fantin et al., "A Novel Mitochondriotoxic Small Molecule [F16] That Effectively Inhibits Tumor Cell Growth," *Cancer Cell*, 2(1), 29-42 (Jul. 2002).*
Cayman Chemicals, "F16" Product Information sheet, Catalog No. 10022, Product Chemical Name is 4[(1E)-2-(1H-indol-3-yl)ethenyl]-1-methyl-pyridinium iodide, Ann Arbor Michigan, Mar. 16, 2006, one page data sheet.*
Herceg Z. & Z.-Q. Wang. Failure of poly(ADP-ribose) polymerase cleavage by caspases leads to induction of necrosis and enhanced apoptosis. Mol. Cell Biol. 19:5124-5133 (1999).
Hirsch, T. et al. The apoptosis-necrosis paradox. Apoptogenic proteases activated after mitochondrial permeability transition determine the mode of cell death. Oncogene 15:1573-1581 (1997).
Geschwind, J.-F. H., et al. Novel therapy for liver cancer: direct intraarterial injection of a potent inhibitor of ATP production. Canc. Res. 62:3909-3913 (2002), (Jul. 15, 2002).
Green, D.R. & Reed, J.C. Mitochondria & apoptosis. Science 281:1309-1312 (1998).

(Continued)

*Primary Examiner*—Shaojia Anna Jiang
*Assistant Examiner*—Lawrence E. Crane
(74) *Attorney, Agent, or Firm*—Law Offices of Albert Wai-Kit Chan, PLLC

(57) ABSTRACT

This invention also provides a method for treating a cancer subject comprising administering to the subject a combination of ATP-depleting agents at concentrations which deplete the ATP level to, or close to, at least 15% of normal in cancer cells wherein at least one of the ATP-depleting agents is a mitochondrial ATP-inhibitor, a methylthioadenosine phosphorylase inhibitor or an inhibitor of De Novo purine synthesis other than 6-Methylmercaptopurine riboside, wherein said composition produces a substantially better effect than a composition without at least one of the ATP-depleting agents: a mitochondrial ATP-inhibitor, a glycolytic inhibitor, a methylthioadenosine phosphorylase inhibitor and an inhibitor of De Novo purine synthesis other than 6-Methylmercaptopurine riboside.

7 Claims, No Drawings

OTHER PUBLICATIONS

Leist, M. et al. Intracellular adenosine triphosphate (ATP) concentration: a switch in the decision between apoptosis and necrosis. J. Exp. Med. 185:1481-1486 (1997).

Lemaire, et al. Inhibition of caspase activity induces a switch from apoptosis to necrosis. FEBS Lett. 425:266-270 (1998).

Martin, D.S., et al. ATP depletion + pyrimidine depletion can markedly enhance cancer therapy: fresh insight for a new approach. Canc. Res. 60:6776-6783 (2000).

Mehmet, H., et al. Relation of impaired energy metabolism to apoptosis and necrosis following transient cerebral hypoxia-ischaemia. Cell Death Differ. 5:321-329 (1998).

Nicotera, P. & Leist, M. Energy supply and the shape of death in neurons and lymphoid cells. Cell Death Differ. 4:435-442 (1997).

Nieminen, A.-L., et al. ATP depletion rather than mitochondrial depolarization mediates hepatocyte killing after metabolic inhibition. J. Am. Phys. 267:C67-C74 (1994).

Nord, L.D., et al. Apoptosis induced in advanced CD8F1-murine mammary tumors by the combination of PALA, MMPR and 6AN precedes tumor regression and is preceded by ATP depletion. Canc. Chemo. Pharm. 40:376-384 (1997).

Sane, A.-T. & Bertrand, R. Caspase Inhibition in camptothecin-treated U-937 cells is coupled with a shift from apoptosis to transient G1 arrest followed by necrotic cell death. Canc. Res. 59:3565-3569 (1999).

Sweet, S. & Singh, G. Accumulation of human promyelocytic leukemic(HL-60) cells at two energetic cell cycle checkpoints. Canc. Res. 55:5164-5167 (1995).

Tsujimoto, Y. Apoptosis and necrosis: intracellular ATP level as a determinant for cell death modes. Cell Death Differ. 4:429-434 (1997).

Hageboutros, A., Judes, G.R., Brennan, J., Green, F., Joffman, J., LaCreta, F.P., Colofiore, J., Martin, D.S., Ozols, R.F., O'Dwyer P.J., Phase I trail of fluorouracil modulation by N-phosphonacetyl-L-aspartate and 6-methylmercaptopurine ribonucleoside. Cancer Chemother. Pharmacol.; 1996, 37(3):229-234.

Kelsen, D., Martin, D.S., Colofiore, J., Sawyer, R., Colt, D., A phase II trial of biochemical modulation using N-phosphonacetyl-L-aspartate, high-dose methotrexate, high-dose 5-fluorouracil, and leucovorin in patients with adenocarcinoma of unknown primary site. Cancer; 1992, 70(7): 1988-1992.

Kemeny, N., Schneider, A., Martin D.S., Colofiore J, Sawyer, R.C., Derby, S., Salvia, B., Phase I trial of N-phosphonacetyl-L-aspartate, methotrexate, and 5-fluorouracil with leucovorin rescue in patients with advanced cancer. Cancer Res.; 1989, 49(16): 4636-4639.

Kemeny, N.E., Schneider, A., Martin, D.S., Phase I trial of PALA, methotrexate, fluorouracil, leucovorin, and uridine rescue in patients with advanced cancer. The use of uridine to decrease fluorouracil toxicity. Cancer Invest.; 1990, 8(2):263-264.

Koutcher, J.A., Alfieri, A.A., Matie, C., Mayer, K.L., Street, J.C., Martin, D.S., Effect of 6-aminonicotinamide on the pentose phosphate pathway: 31P NMR and tumor growth delay studies. Magn. Reson. Med., 1996, 36(6):887-892.

Koutcher, J.A., Alfieri, A.A., Tsai, J.C., Matei, C., Stolfi, R.L., Ballon, D., Martin, D.S., Evaluation of chemotherapy and radiation enhancement and 31P NMR spectral changes induced by biochemical modulation. Cancer Invest., 1997, 15(2)111-120.

Mahmood, U., Street, J.C., Matel, C., Ballon, D., Martin, D.S., Koutcher J.A., in vivo detection by 31P NMR of pentose phosphate pathway block secondary to biochemical modulation. NMR Biomed.; 1996, 9(3):114-120.

Martin DS, Kemeny NE. 1992. Modulation of fluorouracil by N-phosphonacetyl-L-aspartate: a review. Semin. Oncol.; 19(2 Suppl 3):49-55, (Mar. 1992).

Martin, D.S., Kemeny, N.E., Overview of N-phosphonacetyl-L-aspartate + fluorouracil in clinical trials. Semin. Oncol.; 1992, 19(2 Suppl 3):228-233, (Mar. 1992).

Martin, D.S, Stolfi, R.L., Colofiore, J.R., Nord, L.D., Sternberg, S., Biochemical modulation of tumor cell energy in vivo: II. A lower dose of Adriamycin is required and a greater antitumor activity is induced when cellular energy is depressed. Cancer Invest.; 1994, 12(3):296-307.

Martin, D.S., Schwartz, G.K., Chemotherapeutically induced DNA damage, ATP depletion, and the apoptotic biochemical cascade. Oncol. Res.; 1997, 9(1):1-5.

Martin, D.S., Spriggs, D., Koutcher, J.A., A concomitant ATP-depleting strategy markedly enhances anticancer agent activity. Apoptosis; 2001, 6:125-131, 2001.

Martin, D.S. Purine and pyrimidine biochemistry, and some relevant clinical and preclinical cancer chemotherapy research In: G. Powls and R.A. Prough (eds), Metabolism and Action of Anti-Cancer Drugs,91-140. London, Taylor and Francis, 1987.

Martin, D.S., Stolfi, R.L., Sawyer, R.C., Spiegelman, S. Casper, E.S. and Young, C.W. Therapeutic utility of utilizing low doses of N-(phosphonacetyl)L-aspartic acid in combination with 5-fluouroucil; a murine study with clinical relevance. Cancer Res. 43:2317-2321, 1983.

Martin, D.S., Alfieri, A., Koutcher, J.A., et al., Selective-killing of drug-resistant mammary carcinomas by exploiting the tumor cell ATP-viability threshold. Proc. AACR 45:570 (Abstract 2462), 2004.

Martin, D.S., Stolfi, R.L., Colofiore, J.C., Koutcher, J.A., Alfieri, A., Sternberg, S., and Nord, L.D. Apoptosis resulting from anti-cancer agent activity in vivo is enhanced by biochemical modulation of tumor cell energy. In: M. Lavin and D. Walters (eds.) Programmed Cell Death. The Cellular and Molecular Biology of Apoptosis 279-296, New York: Harwood Academic 1993.

Martin, D.S., Stolfi, R.L., Nord, L.D. and Colofiore, J.R. Enhancement of chemotherapeutically-induced apoptosis in vivo by biochemical modulation of poly-(ADP-ribose) polymerase. Oncol. Rep. 3:317-322, 1996.

Martin, D.S Cancer chemotherapy: past is prologue. Mt. Sinai. J. Med. 52:426-434, 1985.

Martin, D.S., Bertino, J.R., and Koutcher, J.A. ATP depletion. + pyrimidine depletion can markedly enhance cancer therapy. Fresh insight for a new approach. Cancer Res. 60:6776-6783, 2000.

Koutcher, J.A., Alfieri, A., Stolfi, R.L., Devitt, M.L., Colofiore, J.R., Nord, L.D., and Martin, D.S. Potentiation of three drug chemotherapy regimen by radiation. Cancer Res. 53:3518-3823, 1993.

Colofiore, J.R., Stofli, R.L., Nord, L.D., and Martin, D.S. On the relationship of ATP-depletion to chemotherapeutically-induced tumor regression. Int. J. Oncol. 7:1401-1404, 1995.

Nord, L.D. Stolfi, R.L., Colofiore, J.R., Martin, D.S., Correlation of retetniton of tumore methylmercaptopurine riboside-5'-phophate with effectiveness in CD8F1 murine mammary tumor regression. Biochem Pharmacol; 1996, 51(5):621-627.

Nord, L.D., Stolfi, R.L., Alfieri, A.A., Netto, G., Reuter, V., Sternberg, S.S., Colofiore, J.R., Koutcher, J.A., Martin, D.S., Apoptosis induced in advanced CD8F1-murine mammary tumors by the combination of PALA, MMPR and 6AN precedes tumor regression and is preceded by ATP depletion. Cancer Chemother. Pharmacol.; 1997, 40:376-384.

O'Dwyer, P.J., Judes, G.R., Colofiore, J., Walczak, J., Hoffman, J., LaCreta F.P., Comis, R.L., Martin, D.S., Ozols, R.F., Phase I trial of flurorouracil modulation by of N-phosphonacetyl-L-aspartate and 6-methylmercaptopurine riboside: optimization of 6-methylmercaptopurine riboside dose and schedule through biochemical analysis of sequential tumor biopsy specimens. J. Natl. Cancer Inst.; 1991, 83(17):1235-1240.

Stolfi, R.L., Martin, D.S., Enhancement of anticancer activity by selective inhibition of rapidly proliferating tissues of the host. Pharmacol. Ther.; 1991, 49(1-2):43-54.

Stolfi, R.L., Colofiore, J.R., Nord, L.D., Martin, D.S., Enhanced antitumor activity of an Adriamycin + 5-fluorouracil combination when preceded by biochemical modulation. Anticancer Drugs; 1996, 7(1):100-104.

Jurkowitz, et al., Adenosine, Inosine, and Guanosine Protect Glial Cells During Glucose Deprivation and Mitochondrial Inhibition: Correlation Between Protection and ATP Preservation. Journal of Neurochemistry, 1998, 71(2):535-548.

Lieberthal, et al., Graded ATP delpetion can cause necrosis or apoptosis of cultured mouse proximal tubular cells. American Physiological Society; 1998, F315-F327.

Lu, et al., Cellular ATP Depletion by LY309887 as a Predictor of Growth Inhibition in Human Tumor Cell Lines. Clinical Cancer Research; Jan. 1, 2000, 5:271-277.

Venkatachalam, et al., Energy Thresholds That Determine Membrane Integrity and Injury in a Renal Epithelial Cell Line (LLC-PK1). J. Clin. Invest.; 1988, 81:745-758, (Mar. 1988).

Anundi, et al., Fructose prevents hypoxic cell death in liver. The American Journal of Physiology; Sep. 1987;253(3 Pt 1):G390-G396.

Cannon, et al., The Effects of Fructose on Adenosine Triphosphate Depletion following Mitochondrial Dysfunction and Lethal Cell Injury in Isolated Rat Hepatocytes. Toxicology and Applied Pharmacology; 1991, 108(3):407-416.

Yager, et al., Correlation between Content of High-Energy Phosphates and Phypoxic-Ischemic Damage in Immature and Mature Astrocytes. Elsevier Science Publishers, Amsterdam; 1994, 82(1-2):62-68, (Oct. 14, 1994).

PCT International Preliminary Examination Report for Sloan Kettering Institute for Cancer Research, PCT/US01/46886, "Treatment of cancer by reduction of intracellular energy and pyrimidines," Filed Dec. 4, 2001, Dated Jul. 25, 2003.

Amarante-Mendes, G.P., Finucane, D.M., Martin, S.J., Cotter, T.G., Salvesen, G.S. and Green, D.R., 1998, "Anti-apoptotic oncogenes prevent caspase-dependent and indepenent commitment for cell death," Cell Death Differ., 5:298-306.

Batova, A., Diccianni, M.B., Omura, Minamisawa, M., Yu, J., Carrera, C.J., Bridgeman, L.J., Kung, F.H., Pullen, J., Amyulong, M.D. and Yu, A.L., 1999, Use of alanosine as a methyladenosine phosphorylase—selective therapy for T-cell acute lymphoblastic leukemia in vitro, Cancer Res., 59:1492-1497.

Berger, N.A., and Berger, S.J., 1986, "Metabolic consequences of DNA damage: The role of poly (ADP-ribose) polymerase as mediator of the suicide response," In: L. Grossman, A.C. Upton, (eds.) Mechanims of DNA Damage and Repair, pp. 357-363. New York: Plenum Publishing Corporation.

Berns, A., May 2002, "Senescence: A companion in chemotherapy?" Cancer Cell, 309-311.

Bertino, J.R., 1990, "Leucovorin rescue revisited: Editorial," J. Clin. Oncol., 8 (2):193-195.

Bissett, D., Mcleod, H.L., Sheedy, B., Collier, M., Pithavala, Y., Paradiso, L., Pitsiladas, M. and Cassidy, J., 2001, "Phase 1 dose-escalation and pharmacokinetic study of a novel folate analogue A G 2034," Br. J. Cancer, 84:308-312.

Bonfoco, E., Krainc, D., Ankarcrona, M., Nicotera, P. and Lipton, S.A., 1995, "Apoptosis and necrosis: two distinct events induced, respectively, by mild and intense insults with N-methyl-D-aspartate or metric oxide/superoxide in cortical cell cultures," Proc. Natl. Acad. Sci. USA, 92:7162-7166.

Bose, R., Verheij, M., Haimovitz-Friedman, A., Scotto, K., Kucks, Z. and Kolesnick, R., 1995, "Ceramide synthase mediates daunorubicin-induced apoptosis: an alternative mechanism for generating death signals," Cell, 82:405-411.

Boulares, A.H., Yokovlev, A.G., Ivanova, V., Stoica, B.A., Wang, G., Iyer, S. and Smulson, M., 1999, "Role of poly (ADP-ribose) polymerase (PARP) cleavage in apoptosis. Caspase-3 resistant PARP mutant increases rates of apoptosis in transfected cells," J. Biol. Chem., 274:22932-22940.

Britten, C.D., Rowinsky, E.K., Baker, S.D., Weiss, G.R., Smith, L., Staphenson, J., Rothenberg, M., Smetzer, L., Cramer, J., Collins, W., Von Hoff, D.D., and Eckhardt, S.G., 2000, "A Phase 1 and pharmacokinetic study of the mitochondrial-specific chodacyanine dye analog MKT 011," Clin. Cancer Res., 6:42-49.

Bronder, J.L. and Moran, R.G., 2002, "Antifolates targeting purine synthesis allow entry of tumor cells into S phase regardless of p53 function," Cancer Res., 62:5236-5241.

Budihardjo, II, Walker, D.L., Svingen, P.A., Buckwalter, C.A., Desnoyers, S., Eckdahl, S., Shah, G.M., Poirier, G.G., Reid, J.M., Ames, M.M., and Kaufmann, S.H., 1998, "6-Aminonicotinamide sensitizes human tumor cell lines to cisplatin," Clinical Cancer Research, 4:117-30.

Cahill, D.P., Kinzler, K.W., Vogelstein, B. and Lengauer, C., 1999, "Genetic instability and Darwinian selection tumors," Trends in Cell Biology, 57-60.

Carson, D.A., Seto, S., Wasson, B., and Carrera, C., 1986, "DNA strand breaks, NAD metabolism, programmed cell death," Exp. Cell. Res., 164:273-281.

Chatterjee, S., Hirota, H., Belfi, C.A., Berger, S.J. and Berger, N.A., 1997, "Hypersensitivity to DNA cross-linking agents associated with up-regulation of glucose-regulated stress protein GRP 78," Cancer Res., 57:5112-5116.

Chen, Z.H., Zhang, H. and Savarese, T.M., 1996, "Gene deletion chemoselectivity: codeletion of the genes for p16INK4, methylthioadenosine phosphorylase, and the _-and _-interferons in human pancreatic cell carcinoma lines and its implications for chemotherapy," Cancer Res., 56:1083-1090.

Constantini, P., Chernyak, B.V., Petronilli, V. and Bernardi, P., 1996, "Modulation of the mitochondrial permeability transition pore by pyridine nucleotides and dithiol oxidation at two separate sites," J. Biol. Chem., 271:6746-6751.

Cory, A.H., and Cory, J.G., 1994, "Use of nucleoside Kinase deficient mouse leukemia L1210 cell lines to determine metabolic routes of activation of antitumor nucleoside analogs," Adv. Enzyme Regul., 34:1-12.

Cotter, T.G., Lenon, S.V., Glynn, J.G. and Martin, S.J., 1990, "Cell death via apoptosis and its relationship to growth, development and differentiation of both tumor and normal cells," Anticancer Res., 10:1153-1160.

Dang, C.V. and Semenza, G.L., 1999, "Oncogenic alterations metabolism," Trends Biochem. Sci., 24:68-92.

Dietrich, L.S., Kaplan, L., and Friedland, I.M., 1958, "Pyridine nucleotide metabolism: mechanism of action of the niacin antagonist, 6-aminonicotinamide," J. Biol. Chem. 233:964-968.

Droin, N., Beauchemin, M., Solary, E. and Bertrand, R., 2000, "Identification of a caspase-2 isoform that behaves as endogenous inhibitor of the caspase cascade," Cancer Res., 60:7039-7047.

Eguchi, Y., Shimizu, S., and Tsujimoto, Y., 1997, "Intracellular ATP levels determine cell fate by apoptosis or necrosis," Cancer Res., 57:1835-1840.

Evtodienko, Y.V., Teplova, V.V., Sidosh, S.S., Ichas, F. and Mazal, J.P., 1996, "Microtubule-active drugs suppress the closure of the permeability transition pore in tumor mitochondria," FEBS Lett., 393:86-88.

Fitchen, J.H., Riscoe, M.K., Dana, B.W., Lawrence, H.J. and Ferro, A.J., 1986, "Methylthioadenosine phosphorylase deficiency in human leukemias and solid tumors," Cancer Res., 46:5409-5412.

Formigli, L., Papucci, L., Tani, A., Schivone, N., Tempestine, A., Orlandini, G.E., Capaccioli, S. and Orlandini, S.Z., 2000, "Aponecrosis: Morphological and biochemical exploration of a syncretic process of cell death sharing apoptosis and necrosis," J. Cell Physiol. 182:41-49.

Forrester, H.B, Albright, N., Ling, C.C. and Dewey, W.C., 2000, "Computerized video time-lapse analysis of apoptosis of REC: Myc cells X-radiated in different phases of the cell cycle," Radiat. Res., 154:625-639.

Gaal, J.C., Smith, K.R., and Pearson, C.K., 1987, "Cellular euthanasia mediated by a nuclear enzyme: A central role for nuclear ADP-ribosylation in cellular metabolism," Trends Biochem. Sci., 12:129-130.

Gewirtz, D.A., 1999, "A critical evaluation of mechanisms of action proposed for the antitumor effects of the anthracycline antibiotics adriamycin and daunorubicin," Biochem. Pharm., 57:727-741.

Goldin, A., Kendetti, J.M., MacDonald, J.S., Muggia, F., Henney, J. and DeVita, V.T., 1981, "Current results of the screening program at the Division of Cancer Treatment, National Cancer Institute," Eur. J. Cancer, 17:129.

Green, D.R., 1998, "Apoptotic pathways: The roads to ruin," Cell, 94:695-698.

Grindey, G.B., Lowe, J.K., Divekey, A.Y., and Halaka, M.T., 1976, "Potentiation by guanine nucleosides of the growth-inhibitory effects of adenosine analogues on L1210 and Sarcoma 180 cells in culture," Cancer Res., 36:379-383.

Haimovitz-Friedman, A., Kan, C.C., Ehleiter, D., Persaud, R.S., McLoughlin, M., Fuks, Z. and Kolesnick, R.N., 1994, "Ionizing radiation acts on cellular membranes to generate ceramide and initiate apoptosis," J.Exp. Med., 180:525-535.

Herceg, Z. and Wang, Z.Q., 1999, "Failure of poly (ADP/ribose) polymerase cleavage by caspases leads to induction of necrosis and enhanced apoptosis," Mol. Cell Biol., 19:5124-5133.

Herken, H., Lange, K. and Kolbe, H., 1969, "Brain disorder induced by pharmacological blockage of the pentose phosphate pathway," Biochem. Biophys. Res. Commun., 36:93-100.

Herter, F., Weissman, S.G., Thompson, H.G. et al., 1961, "Clinical experience with 6-aminonicotinamide," Cancer Res. 21:31-37.

Hickman, J.A., 1992, "Apoptosis induced by anticancer drugs," Cancer Metast. Rev., 11:121-139.

Hunting, D., Gowans, B., and Henderson, J.F., 1985, "Effect of 6-AN on cell growth, poly (ADP-ribose) synthesis and nucleotide metabolism," Biochem. Pharmacol., 34:3999-4003.

Janicke, R.V., Sprengart, M.L., Wati, M.R. and Porter, A.G., 1998, "Caspase-3 is required for DNA fragmentation and morphological changes associated with apoptosis," J. Biol. Chem., 273:9357-9360.

Janicke, R.U., Ng, P., Sprengart, M.L., and Porter, A.G., 1998, "Caspase-3 is required for alpha-fodrin cleavage but dispensable for cleavage of other death substrates in apoptosis," J. Biol. Chem., 273:15540-5.

Jones, M., 1980, "Pyrimidine nucleotide biosynthesis in animals: Genes, enzymes and regulation of UMP synthesis," Ann. Rev. Biochem., 49:253-279.

Kamatani, N., Nelson, Rees, W.A. and Carson, D.A., 1981, "Selective killing of human malignant cell lines deficient in methylthioadenosine phosphorylase, a purine metabolic enzyme," Proc. Natl. Acad. Sci. USA, 78:1219-1223.

Kass, G.E., Eriksson, J.E., Weis, M., Orrenius, S., and Chow, S.C., 1996, "Chromatin condensation during apoptosis requires ATP," Biochem. J., 318:749-52.

Kerr, J.F.R., Wyllie, A.H., and Currie, A.R., 1972, "Apoptosis: a basic biological phenomenon with wide-ranging implications in tissue kinetics," Brit. J. Cancer, 26:239-257.

King, M.P., and Attardi, G., 1989, "Human cells lacking mtDNA: Repopulation with exogenous mitochondria by complementation," Science, 246:500-503.

King, K.L. and Cidlowski, J.A., 1995, "Cell cycle and apoptosis: Common pathways to life and death," J. Cell Biochem., 58:175-180.

Ko et al., 2004, "Advanced cancers: eradication in all cases using 3-bromopyruvate therapy to deplete ATP," Biochemical and Biophysical Research Communications, 269-275.

Kroemer, G., 1997, "Mitochondrial implication in apoptosis. Towards an endosymbiont hypothesis of apoptosis evolution," Cell Death Differ., 4:443-456.

Kroemer, G., Zamzami, N., and Susin, S.A., 1997, "Mitochondrial control of apoptosis," Immunol. Today, 18:44-51.

Krug, L.M., Ng, K.K., Kris, M.G., Miller, V.A., Tong, W., Heelan, R.J., Leon, L., Leung, D., Kelly, J., Grant, S.C. and Sirotnak, F.M., 2000, "Phase I and pharmacokinetic study of 10-propargyt-10-deazaaminopterin a new antifolate," Clin. Cancer Res., 3493-3498.

Kuida, K., Hayder, T.F., Kuan, C.Y., Gu, Y., Taya, C., Karasuyama, H., Su, M.S.S., Radic, P. and Flavell, R.A., 1998, "Reduced apoptosis and cytochrome c- mediated caspase activation in mice lacking caspase activation in mice lacking caspase 9," Cell, 94:325-337.

Lemasters, J.J., 1999, "Necraptosis and the mitochondrial permeability transition: shared pathways to necrosis and apoptosis," Am. J. Physiol., 276:G1-6.

Li, H., Zhu, H., Xu, C.J., 1998, "Cleavage of BID by caspase 8 mediates the mitochondrial damage in the Fas pathway of apoptosis," Cell, 94:491-501.

Li, W.W., Cole, P., Martin, D., Banerjee, D. and Bertino, J.R., 2000, "Methylthioadenosine phosphorylase (MTAP) status determines sensitivity to L-alanosine in human soft tissue sarcoma cell lines and is enhanced by 6-methylmercaptopurine riboside (MMPR)," Proc. Am. Assoc. Cancer Res., 41:240.

Liu, X., Kim, C.N., Yang, J., Jemmerson, R. and Wang, X., 1996, "Induction of apoptotic program in cell-free extracts: requirement for dATP and cytochrome C.," Cell, 86:147-157.

Lowe, S.W., 1995, "Cancer therapy and p53," Curr. Opin. Oncol., 7:547-553.

Marks, D.I., and Fox, R.M., 1991, "DNA damage, poly(ADP-ribosyl)action and apoptotic cell death as a potential common pathway of cytotoxic drug action," Biochem. Pharmacol. 42:1859-1867.

Martin, D.S., Fugman, R.A., Stolfi, R.L. and Hayworth, E., 1975, "Solid tumor animal model therapeutically predictive for human breast cancer," Cancer Chemother. Rep. Part 2, 5:89, Iss. #1, Dec. 1975.

Martin, D.S., Stolfi, R.L., and Colofiore, J.R., 1997, "Perspective: The chemotherapeutic relevance of apoptosis and a proposed biochemical cascade for chemotherapeutically-induced apoptosis," Cancer Invest., 15:372-381.

Martin, D., Matei, C., and Koutcher, J., 2000, "Marked enhancement of radiotherapy-induced tumor regression by an NAD antagonist, 6-aminonicotinamide (6-AN)," Proc. Am. Assoc. Cancer Res., 41:283 (Abstract 1800).

Modica Napolitano, J.S. and Aprille, J.R., 2001, "Delocalized lipophilic cations selectively target the mitochondria of carcinoma cells," Adv. Drug Deliv. Rev., 49:63-701.

National Institute of Health Consensus Development Conference Statement, 2001, "Adjuvant Therapy for Breast Cancer, Nov. 1-3, 2000," J. Natl. Cancer Inst., 93:979-989.

Nguyen, B.T., El Sayed, Y.M., and Sadee, W., 1984, "Interaction among the distinct effects of adenine and guanine depletion in mouse lymphoma cells," Cancer Res., 44:2272-2277.

Nicotera, P. and Leist, M., 1997, "Mitochondrial signals and energy requirement in cell death," Cell Death Differ, 4:516.

Norbori, T., Karras, J.G., Della Ragione, F., Waltz, T.Z., Chen P.P. and Carson, D.A., 1991, "Absence of methylthioadenosine phosphorylase in human gliomas," Cancer Res., 51:3193-3197.

Nobori, T., Szinai, I., Amox, D., Parker, B., Olopade, O.I., Buchhagen, D.L. and Carson, D.A., 1993, "Methylthioadenosine phosphorylase deficiency in human non-small cell lung cancers," Cancer Res., 53:1098-1101.

Presta, M., Rusunati, M., Belleri, M., Morbedelli, L., Ziche, M. and Ribatti, D., 1999, "Purine analogue 6-methylmercaptopurine riboside inhibits early and late phases of the angiogenesis process," Cancer Res., 59:2417-2424.

Raffray, M. and Cohen, G.M., 1997, "Apoptosis and necrosis in toxicology: a continuum or distinct modes of cell death?" Pharmacol. Ther., 75:153-177.

Reed, J.C., 1995, "Regulation of apoptosis by bcl-2 family proteins and its role in cancer and drug resistance," Curr. Opin. Oncol., 7:541-546.

Roy, N., Dveraux, Q.L., Takahashi, R., Salvesen, G.S. and Reed, J.C., 1997, "The c-IAP-1 and c-IAP-2 proteins are direct inhibitors of specific caspases," EMBO J., 16:6914-6925.

Sausville, E.A. and Feigal, E., 1999, "Evolving approaches to cancer drug discovery and development at the National Cancer Institute," USA Ann. Oncol., 10:1287-1291.

Schmitt, C.A. and Lowe, S.W., 2002, "A senescence program controlled by p53 and p16 ink4a contributed to the outcome of cancer therapy," Cell, 109:335-346.

Schmitt, C.A. and Lowe, S.W., 2002, "Apoptosis and chemoresistance in transgenic cancer models," J. Mol. Med., 80:137-146.

Schraufstaffer, I.U., Hinshaw, D.B., Hyslop, P.S., Spragg, R.H., and Cochrane, C.G., 1986, "Oxidant injury of cells DNA strand-breaks activate polyadenosine diphosphate polymerase and lead to depletion of nicotinamide adenine dinucleotide," J. Clin. Invest., 77:1312-1320.

Scudiero, D.A., Monks, A., and Sausville, E.A., 1998, "Cell line designation change: Multidrug-resistant cell line in the NCI anticancer screen," J. Natl. Cancer Inst., 90:862.

Serafino, A., Sinibaldi-Vallebono, P., Lazzarino, G., Tavazzi, B., DiPierro, D., Rosi, G. and Ravagnan, G., 2000, "Modifications of mitochondria in human tumor cells during anthracycline-induced apoptosis," Anticancer Res., 20:3383-3394.

Shantz, G.D., Smith, C.M., Fontanella, L.J., Lau, H.K.F., and Henderson, J.F., 1973, "Inhibition of purine nucleotide metabolism by 6-methylmercaptopurine ribonucleoside and structurally related compounds," Cancer Res., 33:2867-2871.

Shimizu, S., Equchi, Y., Kamike, W., Itoh, Y., Hasegawa, J., Yamabe, K., Otsuid, Y., Matsuda, H. and Tsujimoto, Y., 1996, "Induction of apoptosis as well as necrosis by hypoxia and predominant prevention of apoptosis by bcl-2 and bcl-x," Cancer Res., 56:2161-2166.

Sirotnak, F.M., De Graw, J.I., Colwell, W.T. and Piper, J.R., 1998, "A new analogue of 10-deazaaminopterin with markedly enhanced curative effects against human tumor xenografts in mice," Cancer Chemother. Pharmacal., 42:313-318.

Staunton, M.J. and Gaffney, E.F., 1998, "Apoptosis: basic concepts and potential significance in human cancer," Arch. Pathol. Lab. Med., 122:310-319.

Stolfi, R.L., Martin, D.S. and Fugman, R.A., 1971, "Spontaneous murine mammary adecocarcinoma: Model system for the evaluation of combined methods of therapy," Cancer Chemother. Rep. Part 1, 55:239.

Stolfi, R.L., Stolfi, L.M., Sawyer, R.C., and Martin, D.S., 1988, "Chemotherapeutic evaluation using clinical criteria in spontaneous, autochthonous murine breast tumors," J. Nat. Cancer Inst., 80:52-5.

Street, J.C., Mahmoud, V., Ballon, D., Alfieri, A.A., and Koutcher, J.A., 1996, "13C and 31p NMR investigation of effect of 6-aminonicotinamide on metabolism of RIF-1 tumor cells in vitro," J. Biol. Chem., 271:4113-4119.

Street, J.C., Alfieri, A.A., and Koutcher, J.A., 1997, "Quantitation of metabolic and radiobiological effects of 6-aminonicotinamide in RIF-1 tumor cells in vitro," Cancer Res., 57:3956-3962.

Susin, S.A., Zamzami, N., Castedo, M., Hirsch, T., Marchetti, P., Macho, A., Dauges, E., Gauskens, M. and Kroemer, G., 1996, "Bcl-2 inhibits the mitochondrial release of an apoptogenic protease," J. Exp. Med., 184:1331-1342.

Tanizawa, A., Kubota, M., Hashimoto, H., Shimizu, T., Takimoto, T., Kitoh, T., Akiyama, Y., and Mikama, H., 1989, "VP-16-induced nucleotide pool changes and poly (ADP-ribose) synthesis: The role of VP-16 in interphase death," Exp. Cell Res., 185:237-246.

Tian, W-N., Braunstein, L.D., Apse, K., Pang, J., Rose, M, Tian, X. and Stanton, R.C., 1998, "Importance of Glucose-6-phosphate dehydrogenase activity for cell growth," J. Biol. Chem., 273:10609-10617.

Tian, W-N., Braunstein, L.D., Apse, K., Pang, J., Rose, M., Tian, X., and Stanton, R.C., 1999, "Importance of glucose-6-phosphate dehydrogenase activity in cell death," Am. J. Physiol., 276 (Cell Physiol. 45):C1121-C1131.

Tyagi, A.K. and Cooney, D.A., 1984, "Biomedical pharmacology, metabolism and mechanism of action of L-alanosine, a novel, natural antitumor agent," Adv. Pharmacal. Chemother. 20:69-121.

Warnick, C.T., and Patterson, A.R.P., 1973, "Effect of methylthioinosine on nucleoside concentration in L5158 cells," Cancer Res., 33:1711-1715.

Wielinga, P.R., Reid, G., Challa, E.E., van der Heijden, I., van Deemter, L., De Haas, M., Mol, C., Kuil, A.J., Goeneveld, E., Schuetz, J.D., Brouwer, C., De Abreu, R.A., Wijnholds, J., Bejnen, J.H. and Borst, P., 2002, "Thiopurine metabolism and identification of the Thiopurine metabolites transported by MRP4 and MRP5 overexpressed in human embryonic kidney cells," Mol. Pharm., 62:1321-1331.

Williams-Ashman, H.G., Seidenfeld, J. and Galletti, P., 1982, "Trends in the biochemical pharmacology of 5'- deoxy-5'-methylthioadenosine," Biochem. Pharmacal., 31:277-288.

Woods, R.A., Henderson, R.M., and Henderson, J.F., 1978, "Consequences of inhibition of purine biosynthesis de novo by 6-methylmercaptopurine ribonucleoside in cultured lymphoma L5178 cells," Euro. J. Cancer, 14:765-70.

Wyllie, A.H., 1993, "Apoptosis [The 1992 Frank Rose Memorial Lecture]," Br. J. Cancer., 67:205-208.

Xiang, J., Chao, T. and Korsmyer, S.J., 1996, "Bax-induced cell death may not require interleukin 1-converting enzyme-like proteases," Proc. Natl. Acad. Sci. USA, 93:14359-14563.

Yoshida, H., Kong, Y.Y., Yoshida, R., Elia, A.J., Hakem, R., Penninger, J.M. and Mak, T.W., 1998, "Apaf-1 is required for mitochondrial pathways of apoptosis and brain development," Cell, 94:739-750.

Young, I., Young, G.L., Wiley, J.S. and van der Weyden, M.B., 1985, "Nucleoside transport and cytosine arabinoside (ara C) metabolism in human T lymphoblasts resistant to ara C, thymidine and 6-methyemercap to purine riboside," Eur. J. Cancer Clin. Oncol., 21(9):1077-1082.

Zamzami, N., Susin, S.A., Marchetti, P., Hirsch, T., Gomez-Monterrey, I., Castedo, M., and Kroemer, G., 1996, "Mitochondrial control of nuclear apoptosis (see co=ents]," J. Exp. Med., 183:1533-44.

Zou, H., Li, Y., Liu, X., and Wang, X., 1999, "An apaf-1-cytochrome c multimeric complex is a functional apoptosome that activates procaspase-9," J. Biol. Chem., 274:11549-11556.

European Communications for Sloan-Kettering Institute for Cancer Research, European Application No. 01986104.6, filed Jul. 2, 2003, dated Sep. 6, 2007.

U.S. Office Action for Martin et al., U.S. Appl. No. 10/172,346, filed Jun. 13, 2002, Dated Nov. 19, 2003.

U.S. Office Action for Martin et al., U.S. Appl. No. 10/172,346, filed Jun. 13, 2002, Dated Jun. 15, 2005.

U.S. Office Action for Martin et al., U.S. Appl. No. 10/172,346, filed Jun. 13, 2002, Dated Jun. 15, 2006.

Notice of Allowance and Fee(s) Due and Notice of Allowability, for Martin et al., U.S. Appl. No. 10/172,346, filed Jun. 13, 2002, Dated Aug. 20, 2007.

NIH R01 Grant Information for 1R01CA098505—1A3, PI Jason Koutcher, Project Title "Cytocidal Theraphy in Vivo for Drug-Resistant Tumors," previously submitted for U.S. Appl. No. 10/172,346.

National Cancer Institute Raid Grant Information, PI Maiyer Rizvi, previously submitted for U.S. Appl. No. 10/172,346.

Brown, J.M. and B.G. Wouteres, 2001, "Apoptosis: mediator or mode of cell killing by anticancer agents?" Drug Resistance Updates, 4:129-130.

Schmitt, D.A., and S.W. Lowe, 2001, "Apoptosis is critical for drug response in vivo," Drug Resistance Updates, 4:132-134.

Schmitt, E., Sane, A.T. and R. Bertrand, 1999, "Activation and the role of caspases in chemotherapy-induced apoptosis," Drug Resistance Updates 2:21-29.

Supplementary European Search Report from the European Patent Office for Application No. EP 01 98 6104.6—2123 PCT/US0146886 for Sloan-Kettering Institute for Cancer Research dated Mar. 28, 2007.

* cited by examiner

IN-VIVO ENERGY DEPLETING STRATEGIES FOR KILLING DRUG-RESISTANT CANCER CELLS

This application is a national phase of International Application No. PCT/US03/18716, Filed Jun. 13, 2003, now expired, which is a continuation-in-part of U.S. Ser. No. 10/172,346, Filed Jun. 13, 2002, now U.S Pat. No. 7,381,713. The contents of the preceding applications are incorporated herein by reference in their entireties.

The invention disclosed herein was made with government support under National Cancer Institute RAID Grant Application #153. Accordingly, the U.S. Government has certain rights in this invention.

Throughout this application, various references are referred to. Disclosures of these publications in their entireties are hereby incorporated by reference into this application to more fully describe the state of the art to which this invention pertains.

BACKGROUND OF THE INVENTION AND CANCER RELEVANCE

Drug resistance is the central problem of cancer chemotherapy. Clinically effective combination chemotherapy can cause impressive objective tumor response rates, including complete tumor regressions, but some cancer cells are of lesser sensitivity to the agent (i.e., are drug-resistant), are only damaged, recover, and re-grow. The delayed tumor recurrence yields only a short remission period with little improvement in survival time.

There are many mechanisms of drug resistance. Multiple independent mechanisms of drug resistance may coexist in a population of tumor cells as well as in the same cancer cells, as they arise from multiple genetic changes in single cell clones, and are part of the heterogeneity of the neoplastic process. Mechanisms of drug resistance have been largely identified, and this knowledge has suggested many specific approaches to overcoming one or another type of clinical drug resistance, but these attempts have failed as they also potentiate drug toxicity towards normal tissues.

The therapeutic research strategy for several decades has been that the administration of multiple drugs with different properties and mechanisms of action at optimal doses and intervals should result in cells resistant to one class of drug being killed by another drug in the regimen. However, the extensive, clinical data over these decades has evidenced only a minor impact on treatment outcome along with troublesome and serious toxic side effects (e.g., emesis, diarrhea, alopecia, asthenia, fatigue, myelosuppression, febrile neutropenia requiring hospitalization, neurosensory and neuromotor disturbances, arthralgias and myalgias, heart failure, and treatment-related deaths). Despite the long dismal history of repeated failures to meaningfully improve survival rates by aggressive combination chemotherapy with non-cross-reacting drugs, hope is nevertheless expressed that the future will be different with the new molecularly targeted agents.

However, no matter how many effective mechanistically-different anticancer agents there are, and no matter how superior their therapeutic index, cancer cell demise occurs by only two cell death pathways (necrosis or apoptosis). If the two cell death mechanisms are attenuated by drug resistance mechanisms (e.g. p-glycoprotein and/or glutathione prevent intracellular drug levels reaching concentration levels sufficient to fully activate the necrosis pathway; caspase deletions and endogenous caspase inhibitors prevent completion of apoptosis), these tumor cells are only sublethally injured, recover, and proliferate to kill the patient. The history of the results of these clinical trials is therapeutic equivalence between different combination chemotherapy "doublets" and "triplets". The repeated failures of this approach to overcoming clinical drug resistance—i.e., the lack of clinically relevant differences in overall survival-means only continuance of palliative treatment with decisions tailored individually around such issues as differences in toxicity profiles, patients' age and performance status, and quality of life.

New agents, no matter a new molecular target or superior therapeutic index, can only kill cancer cells if there is completion of the cell death pathways through death's door. In drug-resistant cells, it is not the activation of their cell death pathways by clinically effective anticancer agents that is at fault, but rather pathway completion to death of the cell. This reality suggests that continuance of this failed strategy utilizing only aggressive combination chemotherapy with non-cross-reacting drug-will likely result in-to quote Yogi Berra—"déjà vu all over again".

The above facts suggest the development of a treatment (co-administered with the initiation of activity in the cell death pathways by anticancer agents) that complements and augments the agent-induced initiation of activity in cell death pathways to bring the pathway to completion; namely, to cell death. That treatment, focused on severe ATP depletion, has been developed and proven at the preclinical level, and is about to undergo validation by clinical trial with clinical supplies of the ATP-depleting regimen provided by the NCI RAID grant mechanisms.

Heterogeneous neoplastic cell populations likely contain cancer cells of variable sensitivity to the anticancer agents. Less sensitive cells would not receive enough damage to reduce ATP to low levels sufficient to cause necrotic death. We hypothesized that biochemical modulation to further depress ATP to lower lethal-inducing levels would kill these sublethally-injured cells, augment tumor regressions, and perhaps even yield some cures.

SUMMARY OF THE INVENTION

This invention provides a composition comprising a combination of ATP-depleting agents at concentrations which deplete the ATP level to at least 15% of normal in cancer cells, wherein at least one of the ATP-depleting agents is a mitochondrial ATP-inhibitor, a glycolytic inhibitor, a methylthioadenosine phosphorylase inhibitor, an inhibitor of De Novo purine synthesis other than 6-Methylmercaptopurine riboside, or a combination thereof.

The ATP level is depleted to at least 15% of normal in cancer cells. In some embodiments, it is substantially lower than 15%. For example, the level could be 5% of normal. In a further embodiment, the level is as low as 1%.

This invention also provides a composition comprising an effective amount of a combination of ATP-depleting agents at concentrations which deplete the ATP level to at least 15% of normal in cancer cells, and a pyrimidine antagonist, wherein at least one of the ATP-depleting agents is a mitochondrial ATP-inhibitor, a glycolytic inhibitor, a methylthioadenosine phosphorylase inhibitor, an inhibitor of De Novo purine synthesis other than 6-Methylmercaptopurine riboside, or a combination thereof.

This invention also provides a method for treating a cancer subject comprising administering to the subject a combination of ATP-depleting agents at concentrations which deplete the ATP level to, or close to, at least 15% of normal in cancer cells wherein at least one of the ATP-depleting agents is a mitochondrial ATP-inhibitor, a methylthioadenosine phosphorylase inhibitor, an inhibitor of De Novo purine synthesis other than 6-Methylmercaptopurine riboside, or a combination thereof.

This invention also provides a method for treating a cancer subject comprising administering to the subject a combination of ATP-depleting agents at concentrations which deplete the ATP level to, or close to, at least 15% of normal in cancer cells wherein at least one of the ATP-depleting agents is a mitochondrial ATP-inhibitor, a methylthioadenosine phosphorylase inhibitor, an inhibitor of De Novo purine synthesis other than 6-Methylmercaptopurine riboside, or a combination thereof, wherein said composition produces a substantially better effect than a composition without at least one of the following ATP-depleting agents: a mitochondrial ATP-inhibitor, a glycolytic inhibitor, a methylthioadenosine phosphorylase inhibitor, an inhibitor of De Novo purine synthesis other than 6-Methylmercaptopurine riboside, or a combination thereof.

This invention also provides a method for induction of cancer cell death comprising contacting said cancer cell with a combination of ATP-depleting agents at concentrations which deplete the ATP level to at least 15% of normal in cancer cells wherein at least one of the ATP-depleting agents is a mitochondrial ATP-inhibitor, a methylthioadenosine phosphorylase inhibitor, an inhibitor of De Novo purine synthesis other than 6-Methylmercaptopurine riboside, or a combination thereof.

This invention also provides a method for induction of cancer cell death comprising contacting said cancer cell with a combination of ATP-depleting agents at concentrations which deplete the ATP level to at least 15% of normal in cancer cells wherein at least one of the ATP-depleting agents is a mitochondrial ATP-inhibitor, a methylthioadenosine phosphorylase inhibitor, an inhibitor of De Novo purine synthesis other than 6-Methylmercaptopurine riboside, or a combination thereof, wherein said composition produces a substantially better effect than a composition without at least one of the following ATP-depleting agents: a mitochondrial ATP-inhibitor, a glycolytic inhibitor, a methylthioadenosine phosphorylase inhibitor, an inhibitor of De Novo purine synthesis other than 6-Methylmercaptopurine riboside, or a combination thereof.

This invention provides a method for treating a cancer subject, and for the induction of cancer cell death, comprising administering to the subject a combination of ATP-depleting agents, a pyrimidine antagonist, and anticancer agent to which the treated cancer is sensitive, at concentrations which together collectively deplete the ATP levels to at least 15% of normal in cancer cells wherein at least one of the ATP-depleting agents is a mitochondrial ATP-inhibitor, a glycolytic inhibitors, a methylthioadenosine phosphorylase inhibitor, an inhibitor of De Novo purine synthesis other than 6-Methylmercaptopurine riboside, or a combination thereof.

This invention provides a method for treating a cancer subject, and for the induction of cancer cell death, comprising administering to the subject a combination of ATP-depleting agents, a pyrimidine antagonist, and anticancer agent to which the treated cancer is sensitive, at concentrations which together collectively deplete the ATP levels to at least 15% of normal in cancer cells wherein at least one of the ATP-depleting agents is a mitochondrial ATP-inhibitor, a methylthioadenosine phosphorylase inhibitor, an inhibitor of De Novo purine synthesis other than 6-Methylmercaptopurine riboside, or a combination thereof, wherein said composition produces an effect which is substantially better than a composition without at least one of the following ATP-depleting agents: a mitochondrial ATP-inhibitor, a glycolytic inhibitor, a methylthioadenosine phosphorylase inhibitor, an inhibitor of De Novo purine synthesis other than 6-Methylmercaptopurine riboside, or a combination thereof.

DETAILED DESCRIPTION OF THE INVENTION

Patent Cooperation Treaty (PCT) Application PCT/US01/46886 (International Publication Number WO 02/4720A1) discloses treatment of cancer by reduction of intracellular energy and pyrimidine. Specifically, PCT/US01/46886 highlighted the importance of depletion of ATP in cancer therapy. The disclosure herein provides improvements over this PCT application.

This invention provides a composition comprising a combination of ATP-depleting agents at concentrations which deplete the ATP level to at least 15% of normal in cancer cells, wherein at least one of the ATP-depleting agents is a mitochondrial ATP-inhibitor, a glycolytic inhibitor, a methylthioadenosine phosphorylase inhibitor, an inhibitor of De Novo purine synthesis other than 6-Methylmercaptopurine riboside, or a combination thereof.

The ATP level is depleted to at least 15% of normal in cancer cells. In some embodiments, it is substantially lower than 15%. For an example, the level could be 5 to 10% of normal. In another instance, the level is 1 to 4%. In a further embodiment, the level is as low as 1%.

This invention also provides a composition comprising an effective amount of a combination of ATP-depleting agents at concentrations which deplete the ATP level to at least 15% of normal in cancer cells, wherein at least one of the ATP-depleting agents is a mitochondrial ATP-inhibitor, a glycolytic inhibitor, a methylthioadenosine phosphorylase inhibitor, an inhibitor, of De Novo purine synthesis other than 6-Methylmercaptopurine riboside, or a combination thereof.

This invention also provides the above compositions, wherein said compositions produce a substantially better effect than a composition without at least one of the following ATP depleting agents: a mitochondrial ATP-inhibitor, a glycolytic inhibitor, a methylthioadenosine phosphorylase inhibitor, an inhibitor of De Novo purine synthesis other than 6-Methylmercaptopurine riboside, or a combination thereof.

As used herein, substantially better means that the composition could deplete the intracellular energy level at least 5% better. In another embodiment, the composition is 5% to 100% better. In a separate embodiment, it is 10% to 100% better. In a further embodiment, it is 15% to 100% better. In a still further embodiment, the composition is 20% to 100% better. In a further embodiment, it is 25% to 100% better. In another embodiment, it is 30% to 100% better. In a separate embodiment, it is 35% to 100% better. In another embodiment, it is 40% to 100% better. In a further embodiment, it is 45% to 100% better. In another embodiment, it is 50% to 100% better. In a still further embodiment, it is 55% to 100% better. In a separate embodiment, it is 60% to 100% better. In a still separate embodiment, it is 65% to 100% better. In another embodiment, it is 70% to 100% better. In a separate embodiment, it is 75% to 100% better. In another embodiment, it is 80% to 100% better. In a separate embodiment, it is 85% to 100% better. In a further embodiment, it is 90% to 100% better. Finally, the composition may be 95% to 100% better.

To achieve "substantially better than the composition without", it is not necessary that the depleting agents used be more than one agent. In fact, a single agent may be capable of performing such better effect.

The above compositions may further comprise a pyrimidine depleting agent. Further, the above compositions may comprise an anticancer agent to which the cancer is sensitive. In a still further embodiment, the anticancer agent is at approximately half the maximum tolerated dose.

These agents stated hereinabove may be a single agent but with more than one function. For example, an ATP-depleting agent may also be an anticancer agent.

The ATP-depleting agents include but are not limited to 6-methylmercaptopurine riboside (MMPR), 6-Aminonicotinamide (6-AN) or alanosine (AL).

The above compositions may further comprise N(phosphonacetyl)-L-aspartic acid (PALA). In a separate embodiment of the compositions, it comprises 3-bromopyruvic acid.

The above composition further comprises dehydroepiandrosterone (DHEA), oxythiamine (OT) or in combination thereof.

In an embodiment, the composition further comprises 6-Aminonicotinomide (6-AN).

The above composition may further comprise a cytokine. In an embodiment, the cytokine is G-CSF.

This invention also provides a pharmaceutical composition comprising the above composition and a pharmaceutically acceptable carrier.

For the purposes of this invention, "pharmaceutically acceptable carriers" mean any of the standard pharmaceutical carriers. Examples of suitable carriers are well known in the art and may include, but are not limited to, any of the standard pharmaceutical carriers such as a phosphate buffered saline solution and various wetting agents. Other carriers may include additives used in tablets, granules and capsules, etc. Typically such carriers contain excipients such as starch, milk, sugar, certain types of clay, gelatin, stearic acid or salts thereof, magnesium or calcium stearate, talc, vegetable fats or oils, gum, glycols or other known excipients. Such carriers may also include flavor and color additives or other ingredients. Compositions comprising such carriers are formulated by well-known conventional methods.

This invention also provides the combination of ATP-depleting agents and the anticancer agent to treat drug-resistant cancer cells. In an embodiment, the dose of the anticancer agent is at approximately half of the maximum tolerated dose.

This invention also provide a method for treating a cancer in a subject comprising administering to the subject a combination of ATP-depleting agents at concentrations which deplete the ATP level to, or close to, at least 15% of normal in cancer cells wherein at least one of the ATP-depleting agents is a mitochondrial ATP-inhibitor, a methylthioadenosine phosphorylase inhibitor, an inhibitor of De Novo purine synthesis other than 6-Methylmercaptopurine riboside or combination thereof.

This invention also provides a method for treating a cancer subject comprising administering to the subject a combination of ATP-depleting agents at concentrations which deplete the ATP level to, or close to, at least 15% of normal in cancer cells wherein at least one of the ATP-depleting agents is a mitochondrial ATP-inhibitor, a glycolytic inhibitor, methylthioadenosine phosphorylase inhibitor, an inhibitor of De Novo purine synthesis other than 6-Methylmercaptopurine riboside, or a combination thereof, and said composition produces a substantially better effect than a composition without at least one inhibitor of the following ATP-depleting agents: a mitochondrial ATP-inhibitor, a glycolytic inhibitor, a methylthioadenosine phosphorylase inhibitor, an inhibitor of De Novo purine synthesis other than 6-Methylmercaptopurine riboside or a combination thereof.

This invention also provides the above methods wherein the agents further comprise a pyrimidine-depleting agent.

The above methods may further comprise an anticancer agent. In another embodiment, the cancer is clinically sensitive to the employed anti-cancer agent.

In a separate embodiment, the anticancer agent is at approximately half of the maximum tolerated dose.

This invention also provides a method for induction of cancer cell death comprising contacting said cancer cell with a combination of ATP-depleting agents at concentrations which deplete the ATP level to at least 15% of normal in cancer cells wherein at least one of the ATP-depleting agents is a mitochondrial ATP-inhibitor, a methylthioadenosine phosphorylase inhibitor, an inhibitor of De Novo purine synthesis other than 6-Methylmercaptopurine riboside, or a combination thereof.

This invention also provides a method for induction of cancer cell death comprising contacting said cancer cell with a combination of ATP-depleting agents at concentrations which deplete the ATP level to at least 15% of normal in cancer cells wherein at least one of the ATP-depleting agents is a mitochondrial ATP-inhibitor, a methylthioadenosine phosphorylase inhibitor, an inhibitor of De Novo purine synthesis other than 6-Methylmercaptopurine riboside, or a combination thereof, wherein said composition produces a substantially better effect than a composition without at least one of the following ATP-depleting agents: a mitochondrial ATP-inhibitor, a glycolytic inhibitor, a methylthioadenosine phosphorylase inhibitor, an inhibitor of De Novo purine synthesis other than 6-Methylmercaptopurine riboside, or a combination thereof.

The above methods may comprise a pyrimidine-depleting agent. In an embodiment, the above methods further comprise an anticancer agent.

In an embodiment, the cancer is clinically sensitive to the employed anticancer agent. In a further embodiment, the anticancer agent is at approximately half of the maximum tolerated dose.

This invention provides a method for treating a cancer subject, and for the induction of cancer cell death, comprising administering to the subject a combination of ATP-depleting agents, a pyrimidine antagonist, and anticancer agent to which the treated cancer is sensitive, at concentrations which together collectively deplete the ATP levels to at least 15% of normal in cancer cells wherein at least one of the ATP-depleting agents is a mitochondrial ATP-inhibitor, a glycolytic inhibitors, a methylthioadenosine phosphorylase inhibitor, an inhibitor of De Novo purine synthesis other than 6-Methylmercaptopurine riboside, or a combination thereof.

This invention provides a method for treating a cancer subject, and for the induction of cancer cell death, comprising administering to the subject a combination of ATP-depleting agents, a pyrimidine antagonist, and anticancer agent to which the treated cancer is sensitive, at concentrations which together collectively deplete the ATP levels to at least 15% of normal in cancer cells wherein at least one of the ATP-depleting agents is a mitochondrial ATP-inhibitor, a methylthioadenosine phosphorylase inhibitor, an inhibitor of De Novo purine synthesis other than 6-Methylmercaptopurine riboside, or a combination thereof, wherein said composition produces an effect which is substantially better than a composition without at least one of the following ATP-depleting agents: a mitochondrial ATP-inhibitor, a glycolytic inhibitor, a methylthioadenosine phosphorylase inhibitor, an inhibitor of De Novo purine synthesis other than 6-Methylmercaptopurine riboside, or a combination thereof.

In an embodiment of the above methods, the anticancer agent is at approximately half of the maximum tolerated dose.

The ATP-depleting agents used in the above methods include but are not limited to 6-methylmercaptopurine riboside (MMPR), 6-Aminonicotinamide (6-AN) and alanosine (AL).

In an embodiment of the above methods, the methods further comprise N-(phosphonacetyl)-L-aspartic acid (PALA).

In an embodiment of the above methods, the method further comprises 3-bromopyruvic acid.

In an embodiment of the above methods, the method further comprises N-(phosphonacetyl)-L-aspartic acid (PALA).

In an embodiment of the above methods, the method further comprise dehydroepiandrosterone (DHEA), oxythiamine (OT) or in combination thereof.

In an embodiment of the above methods, the method further comprises 6-Aminonicotinamide (6-AN).

In an embodiment of the above methods, the method further comprises a cytokine. The cytokine includes but is not limited to G-CSF.

This invention also provides a method for killing drug-resistant cancer cells comprising contacting the combination of ATP-depleting agents and the anticancer agent. In an embodiment, the dose of the anticancer agent is at approximately half of the maximum tolerated dosage.

This invention provides a method for treating drug-resistant cancer cells comprising contact the said cancer with a combination of ATP-depleting agents and an anticancer agent.

In an embodiment the dose of said anticancer agent is at approximately half of the maximum tolerated dose.

This invention provides the above method, wherein the ATP level is depleted to at least 15% of normal in cancer cells and at least one of the ATP-depleting agents is a mitochondrial ATP-inhibitor, a glycolytic inhibitor, a methylthioadenosine phosphorylase inhibitor, an inhibitor of De Novo purine synthesis other than 6-Methylmercaptopurine riboside, or a combination thereof.

This invention further provides the above described method wherein the ATP level is depleted to at least 15% of normal in cancer cells and at least one of the ATP-depleting agents is a mitochondrial ATP-inhibitor, a glycolytic inhibitor, a methylthioadenosine phosphorylase inhibitor, an inhibitor of De Novo purine synthesis other than 6-Methylmercaptopurine riboside, or a combination thereof, within and said composition produces an effect which is substantially better than a composition without at least one of the ATP-depleting agents: a mitochondrial ATP-inhibitor, a glycolytic inhibitor, a methylthioadenosine phosphorylase inhibitor, an inhibitor of De Novo purine synthesis other than 6-Methylmercaptopurine riboside or a combination thereof.

Finally, this invention provides method for induction of cancer cell death comprising contacting said cancer cell with an agent capable of inducing necrosis in cancer cells. In an embodiment the agent is an ATP-depleting agent. This method may include a pyrimidine-depleting regimen, or a combination thereof.

The invention will be better understood by reference to the Experimental Details which follow, but those skilled in the art will readily appreciate that the specific experiments detailed are only illustrative, and are not meant to limit the invention as described herein, which is defined by the claims which follow thereafter.

Experimental Details

Map

An ATP-reducing regimen, MAP—an acronym for the combination of 6-methylmercaptopurine riboside, MMPR, +6-aminonicotinamide, 6-AN, +N-(phosphonoacetyl)-L-aspartic acid, PALA)—when co-administered with anticancer agents; e.g., Doxorubicin A (Adriamycin)—enhances experimental tumor regressions in vivo via the necrosis cell death pathway (1). MMPR is an inhibitor of de novo purine biosynthesis that limits adenine supplies for ATP production. (2) 6-AN is an inhibitor of the generation of ATP in the glycolysis pathway (3-6). The cell-killing ATP threshold is 15% of basal levels, and lower (7-8). Since multiple biochemical pathways contribute to the synthesis, generation and maintenance of ATP, a combination of two ATP-depleting agents, MMPR+6-AN, is co-administered with effective anticancer agents to concomitantly block several of the ATP-producing pathways to achieve the ATP-depleting objective of ≦15% of normal. PALA, a de novo pyrimidine biosynthesis inhibitor, can, at low non-toxic dosages, selectively lower pyrimidine nucleotide levels in tumors (9). MMPR+6-AN can markedly lower ATP levels to an average of 15% of normal in murine mammary cancers (1). In the presence of such severely depleted ATP levels the salvage pathway formation of pyrimidine di- and tri-phosphates can be inhibited at the kinase step. Biochemical analysis shows that MAP-treated tumors are severely depleted of two vitally needed metabolites: the UTP pools to 14% of normal (10), and ATP to 15% of normal (1).

Necrosis cell death ensues because intracellular ATP levels at 15% of basal or lower can not sustain cellular homeostasis (7-8, 11-12). Indeed, intracellular ATP levels determine cell fate by apoptosis or necrosis (11) and can effect a "switch" in the cell death mode between apoptosis and necrosis (12). There are many references that anticancer agents that usually cause cell death by apoptosis, when blocked by exogenous or endogenous caspase inhibitors, or by manipulation (i.e., depletion) of energy metabolism, "switch" to necrosis cell death due to severe ATP depletion (references summarized in Table 1).

TABLE 1

EVIDENCE IN NON-DRUG RESISTANT CELLS THAT APOPTOTIC INDUCERS CAN BE MADE TO "SWITCH" TO THE NECROSIS CELL DEATH PATHWAY

| No | Apoptotic Inducer | Cells | Apoptosis Blocker | Result | Reference |
|---|---|---|---|---|---|
| 1 | EGF | Pancreas | Caspase1-inhibitor | Apoptosis to non-apoptotic 'necrotic'-like deaths | FEBS Lett. 491:108-108, 2001 |

TABLE 1-continued

EVIDENCE IN NON-DRUG RESISTANT CELLS THAT APOPTOTIC INDUCERS CAN BE MADE TO "SWITCH" TO THE NECROSIS CELL DEATH PATHWAY

| No | Apoptotic Inducer | Cells | Apoptosis Blocker | Result | Reference |
|---|---|---|---|---|---|
| 2 | Staurosporin, VP-16, Act D | Jurkat Lymphoma T-cell | Inhibitor of caspases | Apoptosis to necrosis | Cell Death Differ. 5:298-306, 1998 |
| 3 | TNF | L929 and HeLa cells | Inhibitor of caspases | Enhanced necrosis | J. Exp. Med, 187:1477-1485, 1998 |
| 4 | Staurosporin, CD95 stimulation | Human T cells | Pre-empted cells of ATP | Apoptosis to necrosis | Cell Death Differ. 4:435-442, 1997 |
| 5 | Fas mAb stimulation | Jurkat T cells, HeLa | ATP depletion | Apoptosis to necrosis | Cancer Res. 57:1835-1840, 1997 |
| 6 | Dexamethasone | B-lymphocytes | Inhibitor of caspases | Apoptosis to necrosis | FEBS Lett. 425:266-270, 1998 |
| 7 | Dexamethasone Etoposide | Thymocytes | Inhibitor of caspases | Apoptosis to necrosis | Oncogene 15:1573-1581, 1997 |
| 8 | Staurosporin, CD95 agonist | Human T cells | Per-empted cells of ATP | Apoptosis to necrosis | J. Exp. Med. 185:1481-1486, 1997 |
| 9 | Deoxycholic acid (activates Fas) | HCT 116 cells | Overexpression on of bcl-2 or PKC | Apoptosis to necrosis | Cancer Lett. 152:107-113, 2000 |
| 10 | $H_2O_2$ | HN U937 cells | Increasing $H_2O_2$ concentration | Apoptosis to necroses | Exp. Cell Res 221:462-469, 1995 |
| 11 | Bax | Jurkat cell | Inhibitor of caspases | Apoptosis to "non-apoptotic" death | Proc Natl Acad Sci. 93:14559, 1996 |
| 12 | Camptothecin | Leukemia U-937 cells | Inhibitor of caspases | Apoptosis to necrosis | Cancer Res. 59:3565-3569, 1999 |
| 13 | Anti-F25 Abs | L 929 cells | Inhibitor of caspases | Apoptosis to necrosis | J. Exp. Med. 188:919-930, 1998 |
| 14 | Anti-F25 Abs | Jurkat cells | Inhibitor of caspases | Apoptosis to necrosis | J. Cell Biol. 143:1353-1360, 1998 |
| 15 | TNF-a | Mouse 3T3 fibroblasts | Inhibitor of caspases | Normally resistant; switch to necrosis | J. Virol. 74:7470-7477, 2000 |

The reason is that anticancer agents usually damage DNA, either directly or indirectly, and thereby activate the two principal pathways of cell death, necrosis and apoptosis, simultaneously in the same cancer cell. Only one death pathway prevails in the cells, as determined by intracellular conditions. However, the two modes of cell death can occur in different cells simultaneously in the same tumor exposed to the same anticancer agent. One reason is that different drug concentrations reach different cancer cells; low concentrations induce apoptosis and high concentrations cause necrotic cell death (13). If the anticancer drug's intracellular concentration is high, the drug-DNA "hit" is then of sufficient magnitude to strongly activate poly (ADP-ribose) polymerase (PARP), and PARP rapidly destroys and depletes glycolytic NAD severely inhibiting the glycolytic production of ATP (1). The resulting severe depletion of ATP causes cell death by necrosis (1). And, although low concentrations of anticancer agents do not damage DNA sufficiently to cause the marked lowering of ATP that results in necrotic cell death, there is still a reduction of ATP. Hence, all effective anticancer agents always cause ATP reduction, and are considered part of our ATP-depleting regimen. An important part, because as "selective" agents for cancer cells, effective anticancer agents preferentially reduce more ATP in cancer cells than normal cells. The agents thereby create a therapeutic opportunity for co-administration of biochemical modulators (i.e., the concomitant addition of an ATP-depleting regimen-e.g., MAP) to further reduce cancer cell ATP to the severely low levels (i.e., ≦15% of normal) that kill, and the cells die a necrotic death.

MAP plus each of ten mechanistically different anticancer drugs at half-MTD (doxorubicin, paclitaxel, docetaxel, cisplatin, phenylalanine mustard, mitomycin C, cyclophosphamide, etoposide, 5-fluorouracil, and radiotherapy) has been demonstrated in vivo to be safe and to cause significantly greater tumor-regressions than the MTD of each anticancer agent alone in hundreds of animals bearing advanced spontaneous and first generation murine breast cancer (references summarized in 1), as well as in murine leukemia and colon tumors. "Cures" (25%) were produced with MAP+radiotherapy in tumor-bearing mice followed for over 380 days (14). The improved therapeutic results were all produced by MAP+each anticancer agent at half-MTD, strongly suggesting that a marked reduction of the toxic side effects of usual MTD clinical cancer chemotherapy will be obtained in future clinical trials.

Spontaneous murine breast cancers have drug-resistant cancer cells as part of their heterogeneous neoplastic cell population just as spontaneously-arising human cancers do. The fact that the number of tumor regressions induced by the combination of MAP+ anticancer agents were always significantly greater than the regressions produced by each anticancer agents alone at MTD suggested that the additional cell kills occurred in drug-resistant cancer cells. Drug-resistant cancer cells are known to be frequently blocked in apoptosis, but not known to have blocks per se in the necrosis cell death pathway. It is likely that drug-resistant cells were killed in the spontaneous tumor because the ATP-depleting strategy is specifically targeted at the latter pathway. However, to obtain a clearer focus of the effect of the ATP-depleting strategy plus an anticancer agent on drug-resistant cancer cells, treatment was done on multi-drug-resistant, overexpressed p-glycoprotein NCI-AR-Res (Adriamycin-resistant) human mammary carcinoma xenografts (15). (See Table 2, below)

MAPAL

As previously noted, the ATP depletion induced in murine mammary tumors by (MMPR+6-AN) of MAP averaged 15% of normal, the cytocidal threshold level of ATP shown to be insufficient to sustain cell viability (7-8). Hence, some individual tumor cells have ATP levels <15% of normal, are killed, and the tumors regress. Other MAP-treated tumors have reduced ATP levels >15% of normal and these tumors are only inhibited in their growth (7). Obviously if the (MMPR+6-AN) induced ATP tumor level had averaged lower than 15% of normal, there would be more tumor cells killed, and more tumor regressions. A stronger ATP-depleting regimen was therefore sought. Alanosine (AL), an inhibitor of de novo adenosine monophosphate synthesis (16), had been previously shown to add to MMPR's reduction of ATP (17). In the latter studies, MMPR alone lowered ATP levels to 49% of normal, and alanosine (AL) alone to 63% of normal, but in combination they decreased ATP to 34% of normal. This striking synergistic reduction of ATP when combined suggested that the addition of AL to MAP(acronym: MAPAL) might safely reduce the average tumor ATP levels still lower than the average 15% of normal induced by MAP. We have not the funding opportunity to compare in the same tumors the average % of induced ATP depletion by MAPAL as compared to MAP. However, the evaluation of MAPAL+an antitumor agent to MAP+the same anticancer agent against advanced mammary tumors in mice showed MAPAL to be therapeutically more effective than MAP, and with no mortality and only an 8% weight loss (unpublished studies).

MAPAL, therefore, was the ATP-depleting regimen chosen to be evaluated against NCI-AR-RES (Adriamycin-resistant) xenografts, and the therapeutic results are summarized in Table 2.

TABLE 2

THE ADDITION OF AN ATP-DEPLETING REGIMAN, MAPAL, ENABLES LO-DOSE ADRIAMYCIN TO KILL DRUG-RESISTANT CANCER CELLS IN ADRIAMYCIN-RESISTANT HUMAN MAMMARY CARCINOMA XENOGRAFTS BY THE NECROSIS CELL DEATH PATHWAY

| Treatment Group$^a$ | $n^c$ | Body Wt change$^c$ % | PR$^c$ % | p-Value$^d$ |
|---|---|---|---|---|
| 1. Control | 20 | +6.6 | 0 | |
| 2. Adria$_{10}$ | 57 | −7.8 | 0 | |
| 3. MAPAL$^b$ | 76 | −3.8 | 18 (14/76) | 0.0003 |
| 4. MAPAL → 2½ hr→ Adria$_5$ | 77 | −7.9 | 48 (37/77) | <.0001 |
| 5. MAPAL + Adria$_5$ (SIMULTANEOUSLY) | 52 | −9 | 46 (24/52) | <.0001 |

$^a$Pooled experiments (99, 103, 108, 112, 114, 115, 116, 117): Nude mice (nu/nu) with NCI-AR-RES mmamry carcinoma xenografts averaged 100 mg when treatment initiated. Indicated treatment administered in three cycles with a 14 day interval between cycles.
$^b$MAPAL = 6-methylmercaptopurine riboside (MMPR$_{150}$) + 6-aminocotinamide (6-AN$_6$) + PALA$_{100}$ + alanosine (AL$_{250}$); subscript = mg/kg. PALA 17 hrs prior to (MMPR + 6 − AN + AL) 2.5 hrs prior to Adria. All agents i.p., except Adria i.v.
$^c$Therapeutic observations recorded one week after the third cource (35 days after initiating therapy.)
. PR = ≧50% decrease in tumor volume
$^d$Compared to Adria$_{10}$Group 2. Comparing Group 3 VS Group 4 =<.0001; VS Group 5, 0.0011

Comment—The combination of MAPAL and Adria (48% PR or 46% PR) is more effective in killing cells than just MAPAL (18% PR), and the use of only half-MTD of Adria in the presence of MAPAL (48% PR or 46% PR) is remarkably more effective in killing drug-resistant cancer than the full dose(MTD) of Adria (0% PR). The striking positive therapeutic results—almost a 50% P.R. rate using a 50% lower dose of Adria (with MAPAL) compared to a 0% P.R. rate with high dose Adria(alone)—auger well for an amelioration of the toxic side effects of high dose Adria in clinical trial along with greater therapeutic results.

It is stressed that there is no difference between the PR rates of Group 4, MAPAL 2½ hours prior to Adria, vs. Group 5, MAPAL simultaneously administered with Adria; namely, 48% P.R. vs. 46% P.R., respectively. It is therefore clear that the time differential (2½ hrs.) did not affect the results; suspicion had been raised that the ATP-dependent p-glycoprotein drug efflux pump might be adversely affected by prior (2½ hr) ATP reduction in Group 4 as the reason for previously published positive therapeutic results with that time interval.

Molecular biology studies (Table 1) demonstrate that the necrosis cell death pathway can fully function (i.e., kill) to bypass a blocked apoptosis pathway, or can be fully evoked following manipulation of energy metabolism to kill cells. The findings in these studies in non-drug resistant cells appear relevant to drug-resistant cells, which are blocked in apoptosis but not known to have blocks per se in the necrosis cell death pathway. Thus, if their apoptosis pathway is blocked but their necrosis pathway is "open", a combination of anticancer agents and ATP-depletion agents should be able to lower ATP to cytocidal levels and selectively kill drug-resistant cells. The findings in these fifteen referenced studies imply that the necrosis cell death pathway could be the therapeutic opportunity to overcome drug-resistant cancer cells.

The primary similarity in the treated cancer cells of these molecular biology studies to drug-resistant cells is that apoptosis activity is prevented in both. In the drug-resistant cells triggered apoptosis cannot proceed to completion because of inherent multiple drug resistance factors; e.g., endogenous caspase inhibitors (so-called IAPs), genetic deletions of caspases, over-expressed anti-apoptotic bcl-2, mutations in p53 and other processing units in the apoptotic program, or in some individual cancer cells the presence of all of these genetically-induced resistance factors. Thus, apoptosis may be triggered (initiated), but not completed, by drug-treatment in the many above-noted molecular biology studies as well as in the drug-resistant cancer cells.

However, there is a significant difference in comparing necrosis pathways. In the molecular biology studies with non-drug resistant cells there are no resistance factors (i.e., obstacles) leading to the necrosis pathway, and the usual apoptosis cell death mode is readily "switched" to necrosis. In contrast, drug-resistant cells can have resistance factors (e.g., drug efflux enzymes) that only allow for low drug concentrations that effect only partial completion of the necrosis pathway). High intracellular drug concentrations are required for cell death by necrosis. Necrosis will not occur unless the drug-target "hit" (usually to DNA) is of sufficient intensity to strongly activate PARP so as to result in a rapid and severe depletion of ATP to cell-killing levels ($\leq 15\%$ of normal). In drug-resistant cancer cells, the drug-induced necrosis pathway is initiated but does not proceed to completion (i.e., to death) because the drug-resistance factors of over-expressed drug efflux pumps (e.g., p-glycoproteins), and/or intracellular drug detoxifiers (e.g., glutathione), lower the intracellular drug level and diminish the drug-target interaction. Hence, although the result is still reduction of ATP, it is not low enough to be lethal-inducing (i.e., $\leq 15\%$ normal ATP). The necrosis pathway is only partially activated, and the ATP depletion does not fall to levels sufficient for cell-killing. Reductions of ATP to above the cell-killing threshold will only cause transient inhibition of cancer cell proliferation followed by complete recovery (7). Thus, following present chemotherapy, drug-resistant cancer cells are only sub-lethally-injured, recover, and grow back to kill the patient.

The molecular biology references (Table 1) suggest that a substantial but non-lethal degree of ATP depletion always occurs in anticancer agent-induced sub-lethally-injured drug-resistant cancer cells because there is only initiation, but not completion (i.e., to death) of the necrosis cell death pathway. Thus, since most effective DNA-damaging anticancer agents are themselves ATP-reducing agents, the further reduction of ATP to the ATP lethality threshold by an ATP-depleting regimen should kill these drug-resistant cells—and does (Table 2). Previous preclinical studies successfully overcoming one or another of the many drug-resistant factors have foundered in the clinical arena because drug-resistant factors are multifactorial. However, the novel ATP-depleting strategy is not aimed at any of the drug-resistant factors, but bypasses them all by directly killing drug-resistant cancer cells through their vulnerable necrosis cell death pathway.

PALM-Bromopyruvate(BrPA)

In non-drug-resistant tumors, Geschwind et al (18) have reported that a potent ATP-depleting agent (3-bromopyruvic acid, or BrPA), when delivered by "direct" intraarterial administration to liver-implanted rabbit tumors, eradicates nearly all viable cancer cells by necrosis, and also without harm to normal cells or to the animals. The absence of mortality and serious toxicity further obviates the notion that severe intra-tumor ATP depletion must be toxic to both normal and cancer cells.

No ATP measurements were reported in the successful cancer cell-killing therapy with BrPA as a single agent. The very high concentration of BrPA achieved by the "direct" arterial delivery apparently depleted ATP in the "directly"-treated cancer cells to cell-killing ATP levels because the same dose of BrPA by systemic i.v. administration only inhibited tumor growth, apparently due to a diluted concentration by the whole blood volume only lowering ATP to levels above the cell-killing ATP threshold, levels shown to effect only inhibition of tumor growth. The level of ATP depletion is all important as regards the therapeutic result (ie, death of cells vs. their transient inhibition). This understanding provides insight for the past failures and present success of ATP-depletion.

Previous attempts at ATP-depletion as therapy have failed due to the lack of understanding of how it would be effective in killing cancer cells. Only recently has there been data establishing that there is a cell-killing ATP threshold of 15% of basal levels and below(7-8), and that attaining this severe lowering of intracellular ATP levels in cancer cells normally requires the concomitant administration of multiple ATP-depleting agents(1).

In line with our planned step by step development of a "best" multiple-ATP-depleting regimen, the incorporation of "selective" antimitochondrial agents (e.g., F16; 19) had been programmed for eventual inclusion in the ongoing development of the new and promising ATP-depleting therapeutic strategy. Although BrPA has not been reported as "selective", it was noteworthy in reducing cellular ATP production via the inhibition of both glycolysis and oxidative phosphorylation (18). It was therefore substituted for the glycolysis inhibitor, 6-AN, in MAPAL. Without 6-AN, MAPAL includes only PALA+Alanosine (AL)+MMPR (acronym: PALM). PALM+BrPA, or PALM–BrPA, inhibits adenine biosynthesis, glycolytic and mitochondrial ATP production. PALM–BrPA+Adria$_5$ vs MAPAL+Adria$_5$ were compared in therapeutic studies in multi-drug-resistant NCI-AR-RES (Adriamycin-resistant) human mammary tumor xenografts. Table 3 pools the data of four experiments.

TABLE 3

PALM-BRPA IS SIGNIFICANTLY SUPERIOR TO MAPAL IN ENHANCING ADRIAMYCIN-DRUG-RESISTANT CANCER CELL KILL. PALM-BRPA INDUCES SEVERE ATP REDUCTION (BY INHIBITING ADENINE BIOSYNTHESIS, GLYCOLYTIC AND MITOCHONDRIAL ATP PRODUCTION) THAT ENABLES LO-DOSE ADRIAMYCIN TO KILL ADRIAMYCIN-RESISTANT CELLS IN HUMAN MAMMARY XENOGRAFTS BY THE NECROSIS CELL DEATH PATHWAY.

| Treatment Group$^a$ | n$^c$ | Body Wt change$^c$ % | Deaths$^c$ % | PR$^c$ % | p-Value |
|---|---|---|---|---|---|
| 1. Control | 8 | +5 | | 0 | |
| 2. Adria$_{10}$ | 15 | −6 | | 0 | |
| 3. MAPAL + Adria$_5$ | 41 | −8 | 4 | 34 | |
| 4. PALM + BrPA$_{10}$ + Adria$_5$ | 42 | −13 | 0 | 62 | $^d$0.01% |

$^a$Four pooled experiments (116, 117, 121, 122): Nude female mice with NCI-AR-Res human mammary carcinoma xenografts averaging 100 mg when treatment initiated. Indicated treatments were administered in 3 cycles with a 14 day interval between cycles.
$^b$MAPAL = MMPR$_{150}$ + 6-AN$_6$ + PALA$_{100}$ + AL$_{250}$. PALM = PALA$_{100}$ + AL$_{250}$ + MMPR$_{150}$. BrPA = 3-Bromopyruvate$_{10}$. All agents i.p., except BrPA and Adria. i.v. Subscripts = mg/kg.
$^c$Therapeutic observation one week after the third course (35 days after initiating therapy). PR = $\geq 50\%$ reduction in tumor size compared to tumor size when treatment initiated. PR % = number PR per group ÷ surviving animals per group × 100.
$^d$Compared to Group 3, MAPAL + Adria$_5$.

Comment—As previously (Table 2), the MTD of Adria, 10 mg/kg, on this Adriamycin-resistant tumor is without tumor-regressing effect (0% PR), whereas Adria. at ½ MTD in the presence of MAPAL causes an impressive number of partial tumor regressions in drug-resistant cells (34% PR), and PALM–BrPA+Adria(½ MTD) is remarkably much more effective (62% PR). With only these four experiments completed, the PALM–BrPA data is considered preliminary. Nevertheless, PALM–BrPA+$Adria_5$ appears to have doubled (62%) the PR rate over MAPAL+Adria (34%). We have not had the funding opportunity to compare the degree of ATP depletion. Both combinations inhibit adenine supplies (i.e., by MMPR), both inhibit adenosine monophosphate biosynthesis (i.e., by AL), and both are glycolytic inhibitors, although by different mechanisms—PALM–BrPA by BrPA, and MAPAL by 6-AN. Although one may be a slightly stronger glycolytic inhibitor, the major difference clearly is that only PALM–BrPA is also a mitochondrial ATP inhibitor. Therefore, it could be anticipated that PALM–BrPA would be the stronger ATP depleter, and the therapeutic results confirm this expectation.

MAP with two ATP depleters effected a tumor ATP average to the cytocidal ATP threshold of 15% of normal (1). MAPAL with three ATP depleters apparently further reduced the average ATP level below this critical cytocidal ATP threshold level. PALM–BrPA with four ATP depleters apparently reduced this critical ATP average still more. Thus, with each incremental decrease in ATP depletion below the cytocidal threshold of 15% of normal, more drug-resistant cancer cells are killed.

Combining a number of ATP-depleting agents sometimes raises concern for anticipated toxic side-effects in normal tissues. However, cancer cells are apparently preferentially vulnerable to ATP depletion, and note that the markedly increased tumor-regressing results of PALM–BrPA, which combines four ATP-depleting components, is not accompanied by gross damage to normal tissues, or mortality.

Other ATP Depleters That Could Contribute to an ATP-Depleting Regimen

A. Inhibitors of Mitochondrial ATP—There are a number of mitochondriotoxic small molecules that selectively accumulate in the mitochondria of tumor cells, compromise their functional integrity, have antiproliferative activity, and can cause a significant depletion of ATP pools. F16 is a small molecule that belongs to this group of compounds that have cancer cell mitochondria as a selective target (19). Although only tumor growth inhibitory as a single agent in vivo, its selectivity and low toxicity suggests that it could make a substantial contribution to ATP depletion as a component of a necrosis-inducing ATP-depleting combination (e.g., MAPAL-F16). F16's selectivity appears restricted to breast cancers. There are other such "selective" mitochondriotoxic molecules that display greater diversity in accumulating in the mitochondria of other types of cancer (20-21), and these should be evaluated in a multi ATP-depleting combination.

B. Inhibitors of Methylthioadenosine Phosphorylase (MTAP)—MTAP is an important intracellular salvage enzyme for adenine (and methionine). Cancer cells that are deficient in MTAP are not able to salvage adenine (and methionine), and are markedly sensitive to inhibitors of the de novo synthesis of adenine nucleotides, especially alanosine which blocks de novo AMP synthesis (22). An inhibitor of MTAP would likely be a useful component of a multi-ATP-depleting combination, because MTAP plays a critical role in recycling adenine moieties from S-adenosylmethionine, derived originally from ATP, back to adenine nucleotide pools (23).

C. Inhibitors of De Novo Purine Synthesis other than 6-Methylmercaptopurine Riboside (MMPR)—all tumors contain genetic instability and alterations, including chromosome losses (i.e., gene deletions) and gains (i.e., overexpressed genes). (24) This genetic instability is reflected in the heterogeneity seen within individual tumors and among tumor of the same type.

Against this background, it is not surprising that MMPR, which requires metabiotic activation by phosphorylation via adenosine kinase (25), meets with resistance in cancers devoid of adenosine kinase (26-27). Since MMPR is an important component of MAPAL and PALM, the ATP-depleting strategy would not be effective in adenosine kinase-deficient cancer cells. Also, cancer cells with overexpressed multidrug resistance protein 4, a drug-efflux pump that transports MMPR out of the cell, would reduce the MMPR intracellular concentration, and be a resistance mechanism (28). Substitution of MMPR in the multi-ATP-depleting regimen by antifolates that target purine synthesis should be as effective as MMPR, might even be better, and should be evaluated. These novel antifolates include DDATHF (29), Agouron compound AG 2034 (30), and PDX (31-32).

REFERENCES

1. Martin, D. S., Bertino, J. R. and Koutcher, J. A. ATP depletion+pyrimidine depletion can markedly enhance cancer therapy: Fresh insight for a new approach. Cancer Res. 60: 6776-6783, 2000.
2. Shantz, G. D., Smith, C. M., Fontanella, L. J., Lau, H. K. F., and Henderson, J. F. Inhibition of purine nucleotide metabolism by 6-methylmercaptopurine ribonucleoside and structurally related compounds. Cancer Res. 33: 2867-2871, 1973.
3. Hunting, D. Gowans, B., and Henderson, J. F. Effect of 6-AN on cell growth, poly (ADP-ribose) synthesis and nucleotide metabolism. Biochem. Pharmacol. 34: 3999-4003, 1985.
4. Street, J. C., Mahmoud, V., Ballon, D., Alfieri, A. A., and Koutcher, J. A. $^{13}$C and $^{31}$P NMR investigation of effect of 6-aminonicotinamide on metabolism of RIF-1 tumor cells in vitro. J. Biol. Chem. 271: 4113-4119, 1996.
5. Street, J. C., Alfieri, A. A., and Koutcher, J. A. Quantitation of metabolic and radiobiological effects of 6-aminonicotinamide in RIF-1 tumor cells in vitro. Cancer Res. 57: 3956-3962, 1997.
6. Koutcher, J. A., Alfieri, A. A., Matei, C., Zakian, K. I., Street, J. C., and Martin, D. S. In vivo $^{31}$p NMR detection of pentose phosphate pathway block and enhancement of radiation sensitivity with 6-aminonicotinamide. Magn. Reson. Med. 36: 887-892, 1996.
7. Sweet, S. and Singh, G. Accumulation of human promyelocytic leukemic (HL-60) cells at two energetic cell cycle checkpoints. Cancer Res. 55: 5164-5167, 1995.
8. Nieminen, A. l., Saylor, A. K., Herman, B., and Lemasters, J. J. ATP depletion rather than mitochondrial depolarization mediates hepatocyte killing after metabolic inhibition. Am. J. Physiol. 267: C67-74, 1994.
9. Martin, D. S., Stolfi, R. L., Sawyer, R. C., Spiegelman, s., Casper, E. S., and Young, C. W. Therapeutic utility of utiliying low doses of N-(phosphonoacetic)-L-aspartic acid in combination with 5-fluorouracil: a murine study with clinical relevance, Cancer Res. 43: 2317-2321, 1983.
10. Martin, D. S., Purine and Pyrimidine Biochemistry, and some relevant clinical and preclinical cancer chemotherapy research. In: G. Powis and R. A. Prough (eds.), Metabolism and Action of Anti-Cancer Drugs, pp. 91-140. London: Taylor and Francis, 1987.
11. Eguchi, Y., Shimizu, S., and Tsujimoto, Y. Intracellular ATP levels determine cell fate by apoptosis or necrosis. Cancer Res., 57: 1835-1840, 1997.
12. Leist, M., Single, B., Castoldi, A. F., Kuknle, S., and Nicotera, P. Intracellular triphosphate (ATP) concentration: A switch in the decision between apoptosis and necrosis. J. Exp. Med., 185: 1835-1840, 1997.
13. Huschtscha, L. I., Anderson, C. E., Bartier, W. A., and Tattersall, M. H. N. Anti-cancer drugs and apoptosis. In: M. Lavin and D. Walters (eds.), Programmed Cell Death, the Cellular and Molecular Biology of Apoptosis, pp. 269-278. New York: Harwood Academic, 1993.
14. Koutcher, J. A., Alfieri, A., Stolfi, R. L., Devitt, M. L., Colofiore, J. R., Nord, L. D., and Martin, D. S. Potentiation of a three drug chemotherapy regimen by radiation. Cancer Res. 53: 3518-3823, 1993.
15. Scudiero, D. A., Monks, A., and Sausville, E. A. Cell line designation change: Multidrug-resistant cell line in the NCI anticancer screen. J. Natl. Cancer Inst. 90: 862, 1998.
16. Tyagic, A. K. and Cooney, D. A. Biomedical pharmacology, metabolism and mechanism of action of L-alanosine, a novel, natural antitumor agent. Adv. Pharmacal. Chemother. 20: 69-121, 1984.
17. Nguygen, B. T., El Sayed, Y. M., and Sadee, W. Interaction among the distinct effects of adenine and guanine depletion in mouse lymphoma cells. Cancer Res. 44: 2272-2277, 1984.
18. Geschwind, J-F. H., Ko, Y. H., Torbenson, M. S., Magee, C., and Pedersen, P. L. Novel therapy for liver cancer: Direct inhibitor of ATP production. Cancer Res, 62: 3909-3913, 2002
19. Fantin, V. R., Berardi, M. J., Scorrano, L., Koromeyer, S. J., and Leder, P. A novel mitochondreotoxic small molecule that selectively inhibit tumor cell growth. Cancer Cell 2: 29-42, 2002
20. Modica Napolitano, J. S. and Aprille, J. R. Delocalizld lipophilic cations selectively target the mitochondria of carcinoma cells. Adv. Drug Deliv. Rev. 49: 63-70, 2001.
21. Britten, C. D., Rowinsky, E. K., Baker, S. D., Weiss, G. R., Smith, L., staphenson, J., Rothenberg, M., Smetzer, L., Cramer, J., Collins, W., Von Hoff, D. D., and Eckhardt, S. G. A Phase 1 and pharmacokinetic study of the mitochondrial-specific chodacyanine dye analog MKT 011. Clin. Cancer Res. 6: 42-49, 2000.
22. Yu, J. Alanosine (UCSD). Curr Opin Investig Drugs 2 (11): 1623-30, 2001.
23. Williams-Ashman, H. G., Seidenfeld, J. and Galletti, P. Trends in the biochemical pharmacology of 5'-deoxy-5'-methylthioadenosine. Biochem pharmacal. 31: 277-288, 1982.
24. Cahill, D. P., Kinzler, K. W., Vogelstein, B., and Lengauer, C. Genetic instability and Darwinian selection in tumors. Trends Biachem. Sci. 59-60, 1999.
25. Martin, D. S. Purine and pyrimidine biochemistry and some relevant clinical and preclinical cancer chemotherapy research, in Metabolism and action of Anticancer Drugs (Powis, G. and Prough, A. R. ds), pp. 91-139, Taylor and Francis, London.
26. Cory, A. H., and Cory, J. G. Use of nucleoside Kinase deficient mouse leukemia L1210 cell lines to determine metabolic routes of activation of antitumor nucleoside analogs. Adv Enzyme Regul 34: 1-12, 1994.
27. Young, I., Young, G. L., Wiley, J. S., and van der Weyden, M. B. Nucleoside transport and cytosine arabinoside (ara C) metabolism in human T lymphoblasts resistant to ara C, thymidine and 6-methyemercap to purine riboside. Eur J Cancer Clin Oncol 21(9): 1077-82, 1985.
28. Wielinga, P. R., Reid, G., Challa, E. E., van der Heijden, I., van Deemter, L., De Haas M., Mol, C., Kuil, A. J., Groeneveld, E., Schuetz, J. D., Brouwer, C., De Abreu, R, A., Wijnholds, J., Bejnen, J. H., and Borst, P. Thiopurine metabolism and identification of the Thiopurine metabolites transported by MRP4 and MRP5 overexpressed in human embryonic kidney cells. Mol. Pharm, 62: 1321-1331, 2002.
29. Bronder, J. L. and Moran, R. G. antifolates targeting purine synthesis allow entry of tumor cells into S phase regardless of p53 function. Cancer Res. 62: 5236-5241, 2002.
30. Bissett, D., Mcleod, H. L., Sheedy, B., Collier, M., Pithavala, Y., Paradiso, L., Pitsiladas, M. and Cassidy, J. Phase 1 dose-escalation and pharmacokinetic study of a novel folate analogue A G 2034. Br. J. Cancer 84: 308-312, 2001.
31. Sirotnak, F. M., De Graw, J. I., Colwell, W. T., and Piper, J. R. A new analogue of 10-deazaminopterin with markedly enhanced curative effects against human tumor xenografts in mice. Cancer Chemother Pharmacal 42: 313-318, 1998.
32. Krug, L. M., Ng, K. K., Kris, M. G., Miller, V. A., Tong, W., Heelan, R. J., Leon, L., Leung, D., Kelly, J., Grant, S. C., and Sirotnak, F. M. Phase I and pharmacokinetic study of 10-propargyt-10-deazaminopterin a new antifolate. Clin Cancer Res: 3493-3498, 2000.

ATP-Depleting Combination (i.e., the ATP-depleting combination that, when co-administered with an anticancer agent effective against the target cancer, achieves cell-killing levels of ATP in drug-resistant cancer cells with the least toxicity to white blood cells and nerves.)

1. The initially employed ATP-depleting agents—6methylmercaptopurine riboside (MMPR)+6-aminonicotinamide (6-AN)—were administered in combination with N-(phosphonacetyl)-L-aspartic acid (PALA), and received the acronym: MAP. MAP enhanced anticancer agent activity against drug-resistant cancer cells.
2. Subsequently, MMPR and 6-AN were combined with alanosine (AL), and received the acronym:MAPAL (i.e., MMPR+6-AN+PALA+AL). MAPAL proved a more effective ATP-depleting agent than MAP. In in vivo studies in tumor-bearing animals, MAPAL, when co-administered with anticancer agents, evidenced greater anticancer activity than MAP, but with occasional evidence of greater myelotoxicity. MAPAL, nevertheless, is better than MAP.
3. The combination of PALA+AL+MMPR without 6-AN (acronym: PALM), when co-administered with anticancer agents, appears to produce the same or better antitumor activity than MAPAL without this occasional toxicity. MAPAL needs to be compared with PALM under the same conditions.
4. 6-AN inhibits glycolysis (1), a desirable ATP-depleting effect since the vast majority of solid cancers depend on glycolysis as a source of ATP (2). 6-AN acts by inhibiting the oxidative portion of the Pentose Phosphate Pathway (PPP) via inhibition of the second enzyme of the PPP. DHEA (dehydroepiandrosterone) inhibits the first enzymes of the oxidated version of the PPP, and, although inferior as an inhibitor of glycolosis to 6-AN is less toxic than 6-AN. But since the glycolytic production of ATP receives substrate contributions (fructose-6-phosphate and glyceraldehyde-3-phosphate) from the PPP, the oxidative portion of the PPP, DHEA will likely produce the same inhibition of glycolysis when administered in combination with an inhibitor of the non-oxidative portion of the PPP, oxythiamine (OT). Thus, PALM+DHEA+OT; acronym: PALMDOT.

Nevertheless, a greater blockade of the PPP might be accomplished by inhibiting both the first and the second enzymes of the oxidative portion of PPP with DHEA+6–AN administration together with simultaneous inhibition of the non-oxidative portion of the PPP by OT; acronym: MAPALDOT. (If MAPALDOT is myelosuppressive, it may be made safe by a co-administration of G-CSF while affecting greater ATP depletion than PALMDOT.) PALMDOT and MAPALDOT need comparison.

Evaluation of the Differences Between ATP-Depleting Regimens of MAPAL, PALM, PALMDOT and MAPALDOT Tumor Differences—Different tumor types (e.g., breast cancer vs. ovarian cancer vs. pancreatic cancer) may differ materially in the quantitative contribution of ATP they receive from different ATP-producing metabolic pathways (e.g., from glycolysis as compared to de novo purine metabolism). If the major contribution is, for example, from de novo purine synthesis, then it may be best to employ PALM as the ATP-depleting regimen, for PALM has two inhibitors of de novo purine synthesis, AL (alanosine) and MMPR (6-methyl-mercaptopurine riboside), and no antiglycolysis component. However, while there are exceptions, the vast majority of solid cancers depend on glucose through glycolysis as an energy source, and it would be imprudent to neglect this information. Hence, there should be evaluation of MAPAL, which contains not only MMPR and AL, but also has 6-AN, a proven inhibitor of glycolysis via the oxidative portion of the Pentose Phosphate pathway (PPP). But 6-AN may have toxicities that are non-pertinent to the goal of ATP depletion (such as rare neuroparalyis) and, therefore, it may be best to use DHEA, a less toxic inhibitor of the oxidative PPP. DHEA may be inferior to 6-AN as an inhibitor of glycolytic ATP production, but DHEA and 6-AN have not been previously compared in regard to reduction of glycolytic ATP, and the combination of DHEA+an inhibitor for the non-oxidative portion of the PPP, OT (oxythiamine), has not been evaluated (in combination) as regards inhibition of glycolytic ATP production.

Greater understanding of the above potential interrelationships may be obtained by comparative studies on three different cancers (the human breast cancer xenograft resistant to Adriamycin, the NCI/Adr-Res; the cisplatin (DDP) -doxorubicin-resistant human ovarian cancer xenograft, the SKOV-3; and the S2 (TXT), a taxotere (TXT)-resistant human pancreatic cancer xenograft) as follows:

1. Controls
2. Cisplatin (DDP) MTD
3. Doxorubicin (DOX) MTD
4. Taxotere (TXT) MTD
5. MAP
6. MAPAL
7. PALM
8. PALMDOT
9. MAPALDOT
10. DDP half-MTD
11. DOX half-MTD
12. TXT half-MTD
13. MAP+DDP half-MTD; +DOX half-MTD; TXT half-MTD
14. MAPAL+DDP half-MTD; +DOX half-MTD; +TXT half-MTD
15. PALM+DDP half-MTD; DOX half-MTD; +TXT half-MTD
16. PALMDOT+DDP half-MTD; +DOX half-MTD; +TXT half-MTD
17. MAPALDOT+DDP half-MTD; +DOX half-MTD; +TXT half-MTD (The above 27 groups (10 tumor-bearing animals per group) cannot, practically-speaking, be included in a single transplant experiment, but can be judiciously covered in a number of smaller experiments.)

Myelotoxicity Differences—None of the above three anticancer agents alone at half-MTD, nor the various ATP-depleting regimens alone, cause myelosuppression in their tumor-bearing mice, but in combination (as in groups 13-17) occasionally do, including a rare fatality which can be prevented by either pyruvate administration, or omission of 6-AN, as in PALM. The indirect evidence, (myelosuppression only in combination, prevention by omission of 6-AN, or administration of pyruvate) suggests an adverse effect to a metabolic step of the glycolysis pathway in either the progenitor bone marrow cells or the peripheral blood leucocytes (PBL). Therefore, before treatment, and at intervals (24, 48, 72, and 96 hours) after treatment, bone marrow and PBL will be analyzed for changes in various steps of glycolysis and the PPP. An understanding of the changes may make it possible to identify a biomarker in glycolysis that will predict which tumor-bearing animal (i.e., patient) will undergo severe neutropenia and make possible early G-CSF administration for prevention as opposed to treatment by G-CSF. Such a biomarker in PBL might be glucose-6-phosphate dehydrogenase, known to be important for cell growth and in cell death(3-4).

The elaborate analysis of "best" ATP-depleting regimens, and control of PBL toxicity, detailed above is warranted by the importance of the drug resistance problem. Combination chemotherapy has been proven to cure the heterogeneity of a few types of cancer (e.g., testicular cancer), so there is clear evidence that it is possible to cure cancer with chemotherapy. But chemotherapy fails to cure most solid cancers because of drug resistance. Since there is strong scientific evidence in support of the ATP-depleting therapeutic strategy to circumvent drug resistance, the elaborate evaluation as planned above is because a careful application in the clinic of preclinical guidelines should enable clinical validation of the pre-clinically-proven strategy. Success is important, for the circumvention of drug resistance factors will clear the way for chemotherapeutic cure of many cancers.

REFERENCES

1. Street, J. C., Mahmoud, U., Ballon, D., Alfieri, A. A., and Koutcher, J. A. 13C and 31P NMR investigation of effect of 6-aminnicotinamide on metabolism of RIF-1 tumor cells in vivo. J. Biol. Chem. 271: 4113-9, 1996.
2. Dang, C. V. and Semenza, G. L. Oncogenic alterations of metabolism. Trends Biochem. Sci. 24: 68-92, 1999.
3. Tian, W-N., Braunstein, L. D., Pang, J., Stuhlmeier, K. M., Xi, Q-C., Tian, X., and Stanton, R. C. Importance of Glucose-6-phosphate dehydrogenase activity for cell growth. J. Biol. Chem. 273: 10609-10617, 1998.
4. Tiam, W-N., Braunstein, L. D., Apse, K., Pang, J., Rose, M., Tian, X., and Stanton, R. C. Importance of glucose-6-phosphate dehydrogenase activity in cell death. Am. J. Physiol. 276 (Cell Physiol. 45): C1121-C1131, 1999.

An ATP-Depleting Regimen (e.g., MAPAL)+an Anticancer Agent (e.g., Taxotere) Induces Permanent Growth Arrest and a Senescence-Like Phenotype in Advanced Human Breast Cancer Xenografts (MDA-MB-468) that Results in Cure.

The induction of cell senescence, along with apoptosis, and other types of cell death (e.g., necrosis, mitotic catastrophe), can be a major response of cancer cells to cytotoxic and cytostatic agents. Thus, treatment conversion of cancer cells to senescent permanent proliferation arrest and subsequent cell death can add an important determinant of effective treatment outcome.

Neither the anticancer agent at MTD, nor the anticancer agent at half-MTD alone, nor the ATP-depleting regimen alone, effected senescence in the breast tumor xenografts. Therefore, this identification that only the combination of the ATP-depleting regimen with a moderate dose of anticancer agent can induce or facilitate senescence in tumor cells is an important finding for the improvement of cancer therapy.

Present Status of Cancer Chemotherapy and Drug Resistance

Chemotherapy is the primary treatment once cancer becomes systemic (i.e., metastasizes). Most anticancer agents damage DNA in their target cancer cells, but the post-damage responses of apoptosis, necrosis, mitotic catastrophe and senescence are thwarted in drug-resistant cancer cells. The drug resistance factors are multiple, and range from mechanisms that limit the drug-target interaction (e.g., overexpression of drug efflux pumps, as p-glycoprotein, and intracellular detoxifiers, as glutathione) to genetic disruption of the apoptotic and senescence pathways. Drug-induced senescence, although difficult to induce, is increasingly being considered an important consequence of effective treatment(2,3). Mitotic catastrophe is a form of programmed cell death when the DNA-damaged cells exit a cell cycle arrest and undergo fatal endomitosis(1). It is the contribution of apoptosis to therapy-induced cell death (the "apoptosis concept" that is considered by most as the pivotal response program in drug-treated tumor cells (4). And necrosis, although occasionally listed as a drug-induced response, is usually not considered.

Yet, necrosis is the cell death pathway simultaneously initiated with apoptosis by drug-induced DNA damage that, unlike apoptosis, can be restored to the completion of cell death (5). Necrosis is due to severe ATP depletion (15% of normal and below), a cell-killing level prevented from attainment by drug-resistant factors (5). However, ATP is nevertheless reduced due to the activation of PARP by anticancer agent-induced DNA damage (5). Thus, unlike "mitotic catastrophe" and the cell death mode of apoptosis, which are initiated but not completed in drug-resistant cancer cells, the necrosis pathway in drug-resistant cells is partially completed (5). The anticancer agent-induced DNA damage, even though lessened by drug-resistant factors, reduces ATP and thereby "chemosensitizes" the drug-resistant cancer cell for further reduction to cell-killing ATP levels by the co-administration of an appropriate ATP-depleting regimen (5). It does not matter whether one or multiple drug-resistant factors are involved in the limitation of the necrosis pathway because the treatment to circumvent the drug-resistant factors is aimed at bringing the product of their collective blocking action—i.e., the reduced ATP level—to cell-killing levels. The ability to kill drug-resistant cancer cells by an apoptotic independent mechanism—i.e., necrosis—has been preclinically demonstrated, and is receiving NCI support for validation of the ATP-depleting strategy by clinical trial.

As noted above, there is growing evidence that senescence of cancer cells can be induced following chemotherapy and can contribute to the success of chemotherapy (2,3). It is of great additional interest that the same ATP-depleting strategy that enhances cancer cell death by inducing necrosis, also can induce senescence in cancer cells in vivo. (The latter gratifying results require additional confirmation in other tumor models and with other anticancer agents.)

Chemotherapy has cured a few types of human tumors. However, many human advanced solid cancers respond poorly to chemotherapy because of drug-resistant cells. The ATP-depleting strategy could circumvent the latter problem, and thereby create the opportunity for chemotherapeutic cure of the more common human malignancies. The belief, and general consensus that chemotherapy kills by apoptosis, and therefore that cells resistant to apoptosis are resistant to drug therapy, neglects the long-established fact that chemotherapy also kills by necrosis (5-7), and overlooks the evidence that cell death by blocked apoptosis can be "switched" to necrosis (7-9). Overcoming drug resistance is the most important obstacle to the success of chemotherapy in the cure of advanced human cancers.

REFERENCES

1. King, K. L. and Cidlowski, J. A. Cell cycle and apoptosis: common pathways to life and death. J. Cell Biochem 58: 175-180, 1995.
2. Berns, A. Senescence: A companion in chemotherapy? Cancer Cell: May, 2002; 309-311.
3. Schmitt, C. A., Fridman, J. S., Yang, M., Lee, S., Baranov, E., Hoffman, R. M., and Lowe, S. W. A senescence program controlled by p53 and p16 ink4a contributed to the outcome of cancer therapy. Cell 109: 335-346, 2002.
4. Schmitt, C. A. and Lowe, S. W. Apoptosis and chemoresistance in transgenic cancer models. J. Mol. Med. 80: 137-146, 2002.
5. Martin, D. S., Bertino, J. R., and Koutcher, J. A. ATP depletion+pyrimidine depletion can markedly enhance cancer therapy: Fresh insight for a new approach. Cancer Res. 60: 6776-6783, 2000.
6. Eguchi, Y., Shimizu, S., and Tsujimoto, Y. Intracellular ATP levels determine cell fate by apoptosis or necrosis. Cancer Res. 57: 1835-1840, 1997.
7. Leist, M., Single, B., Castoldo, A. F., Kuknle, S., and Nicotera, P. Intracellular triphosphate (ATP) concentration: a switch in the decision between apoptosis and necrosis. J. Exp. Med. 185: 1481-1486, 1997.
8. Sane, A. T., and Bertrand, R. Caspase inhibition in camptothecin-treated U-937 cells is completed with a shift from apoptosis to transient G1 arrest followed by necrotic cell death. Cancer Res., 59: 3565-3569, 1999.
9. Lemaire, C., Andreau, K., Souvannavong, K., and Adam, A. Inhibition of caspase activity induced a switch from apoptosis to necrosis. FEBS Lett. 425: 266-270, 1998.

What is claimed is:

1. A pharmaceutical composition comprising an effective amount of N-(phosphonacetyl)-L-aspartic acid (PALA), alanosine (AL), 6-methylmercaptopurine riboside (MMPR), and 3-bromopyruvate (BrPA), in combination with a pharmaceutically acceptable carrier.

2. The composition of claim 1, further comprising adriamycin.

3. The composition of claim 2, wherein the amount of adriamycin is one-half the maximum tolerated dosage.

4. A method for treating a subject having breast cancer, comprising administering to the subject the following agents:
   (i) N-(phosphonacetyl)-L-aspartic acid (PALA);
   (ii) alanosine (AL);
   (iii) 6-methylmercaptopurine riboside (MMPR); and
   (iv) 3-bromopyruvate (BrPA).

5. The method of. claim 4, wherein the agents are administered concurrently or sequentially.

6. The method of 4 further comprising administration of adriamycin.

7. The method of 6, wherein the amount of adriamycin administered is one-half the maximum tolerated dosage.

* * * * *